(12) United States Patent
Uang et al.

(10) Patent No.: US 9,193,743 B2
(45) Date of Patent: Nov. 24, 2015

(54) METHOD OF ENANTIOSELECTIVE ADDITION TO IMINES

(71) Applicant: National Tsing Hua University, Hsinchu (TW)

(72) Inventors: Biing-Jiun Uang, Hsinchu (TW); Wei-Ming Huang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/574,764

(22) Filed: Dec. 18, 2014

(65) Prior Publication Data

US 2015/0183811 A1    Jul. 2, 2015

(30) Foreign Application Priority Data

Dec. 30, 2013   (TW) .............................. 102149092 A

(51) Int. Cl.
*C07F 9/36* (2006.01)
*C07F 3/06* (2006.01)

(52) U.S. Cl.
CPC .... *C07F 9/36* (2013.01); *C07F 3/06* (2013.01)

(58) Field of Classification Search
CPC ................ C07F 9/46; C07F 9/36; C07F 3/06; C07C 209/52
See application file for complete search history.

(56) References Cited

U.S. PATENT DOCUMENTS 8,304,581 B2 * 11/2012 Uang et al. .................... 568/312
8,461,371 B2 *  6/2013 Uang et al. .................... 560/37

* cited by examiner

*Primary Examiner* — Brian J Davis
(74) *Attorney, Agent, or Firm* — Muncy, Geissler, Olds & Lowe, P.C.

(57) ABSTRACT

The present invention relates to a method of enantioselective addition to imines, including: reacting $R_2CH\!\!=\!\!NY$ with $R_3ZnR_4$ in the presence of a compound represented by the following formula (I),

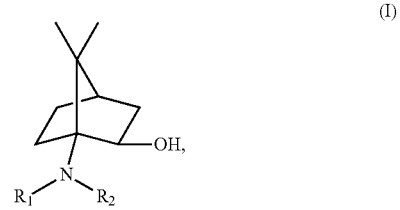

(I)

in which Y, $R_1$, $R_2$, $R_3$ and $R_4$ are defined the same as the specification. Accordingly, the present invention can prepare secondary amines in high yields and enantiomeric excess by the above-mentioned method.

10 Claims, No Drawings

METHOD OF ENANTIOSELECTIVE ADDITION TO IMINES

CROSS REFERENCE TO RELATED APPLICATION

This application claims the benefits of the Taiwan Patent Application Serial Number 102149092, filed on Dec. 30, 2013, the subject matter of which is incorporated herein by reference.

BACKGROUND OF THE INVENTION

1. Field of the Invention

The present invention relates to a method of enantioselective addition to imines and, more particularly, to a method of enantioselective addition of organozinc to imines using a chiral β-amino alcohol.

2. Description of Related Art

Most of isolated natural products have specific stereochemistry. Most of the time, various stereoconfiguration of compounds also causes significant difference in bioactivity. Particularly, stereoconfiguration is critical for most medical compounds or drugs. For example, thalidomide, a chiral molecule, is used for treating sickness and faintness of pregnant women, but the enantiomer thereof causes abnormal fetal development. Furthermore, S, S-isomer of captopril is effective for treatment of hypertension and heart disease. In addition, S-isomer of Dopa can be used for treatment of Parkinson's disease, but R-isomer thereof has toxicity. The U.S. Food and Drug Administration, in 1992, issued an instruction that optical isomers of the medical compounds having chiral center(s) should be isolated from each other, studied separately for their bioactivity, and taken for clinical testing respectively. Moreover, only the therapeutically active isomer of the optical isomers can be brought to market. Accordingly, many scientists focus their research on the improvement of enantioselectivity to obtain substances having specific stereoconfiguration. According to these research results, it is known that the enantioselect ivity of products may be enhanced by the application of chiral reagents, chiral auxiliaries, or chiral catalysts. Through the assistance of the chiral compounds illustrated above, products of high enantioselectivity with high purity can be synthesized.

It is known that chiral amines play important roles in the synthesis of bioactive substances and medical compounds. For example, methoxyphenamine is a β-adrenergic receptor agonist and can be used to treat asthma; rivastigmine is a pseudo-irreversible inhibitor of cholinesterase and can be used to treat Alzheimer's disease; tamsulosin is a selective $\alpha_1$-adrenoceptor antagonist and can be used to decrease urinary symptoms caused by prostate hypertrophy; and repaglinide can stimulate the release of insulin from the pancreas to reduce blood glucose and thus can be used in treating type II diabetes.

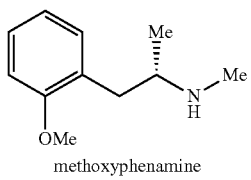

methoxyphenamine

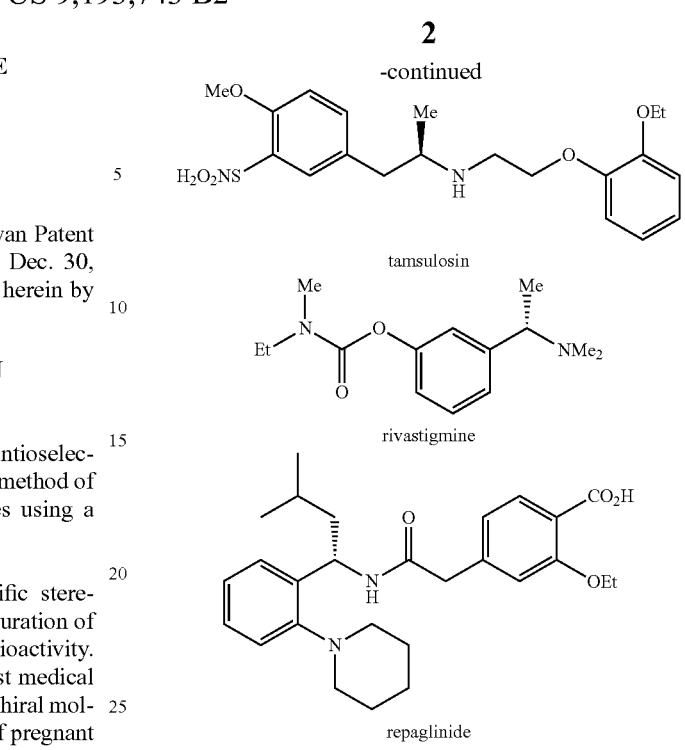

tamsulosin rivastigmine repaglinide

Accordingly, it is an important object of the present invention to develop a method for preparing amine products in high optical purity.

SUMMARY OF THE INVENTION

The object of the present invention is to provide a method of enantioselective addition to imines so as to synthesize amine products in high optical purity.

To achieve the object, the present invention provides a method of enantioselective addition to imines, including: reacting $R_2CH=NY$ with $R_3ZnR_4$ in the presence of a compound represented by the following formula (I),

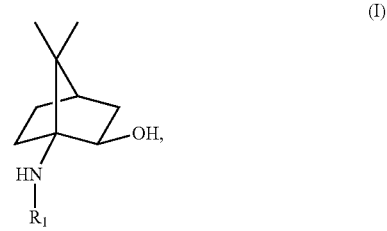

wherein $R_1$ is alkyl, or $R_6$; each of $R_2$, $R_3$, and $R_4$ independently is alkyl, alkenyl, cycloalkyl, cycloalkenyl, heterocycloalkyl, heterocycloalkenyl, aryl, or heteroaryl; and Y is $P(O)Ph_2$; wherein $R_5$ and $R_6$ is selected from the group comprising cycloalkyl, cycloalkenyl heterocycloalkyl, heterocycloalkenyl, aryl, and heteroaryl.

Accordingly, during the above-mentioned reaction, the compound represented by the formula (I) can be an auxiliary for enantioselective addition of organozincs (i.e. $R_3ZnR_4$) to imines (i.e. $R_2CH=NY$). That is, the compound represented by the formula (I) can enhance enantioselectivity of the addition, and the addition product represented by one of the following formulas (II-1) and (II-2) may be prepared in the majority:

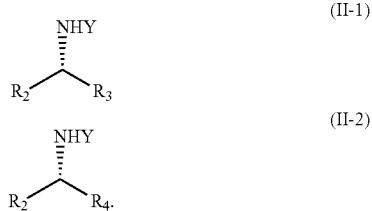

In the present invention, the term "alkyl" refers to a straight or branched hydrocarbon. Examples of alkyl include, but are not limited to, methyl, ethyl, n-propyl, i-propyl, n-butyl, i-butyl, and t-butyl.

In the present invention, the term "alkenyl" refers to a straight or branched hydrocarbon containing one or more double bonds. Examples of alkenyl include, but are not limited to, ethenyl, propenyl, allyl, and 1,4-butadienyl.

In the present invention, the term "cycloalkyl" refers to a saturated hydrocarbon ring system. Examples of cycloalkyl include, but are not limited to, cyclopropyl, cyclobutyl, cyclopentyl, cycloheptyl, and cyclooctyl.

In the present invention, the term "cycloalkenyl" refers to a non-aromatic hydrocarbon ring system having one or more double bonds. Examples of cycloalkenyl include, but are not limited to, cyclopentenyl, cyclohexenyl, and cycloheptenyl.

In the present invention, the term "heterocycloalkyl" refers to a saturated hydrocarbon ring system having one or more ring heteroatoms (e.g., N, O, S or Se). Examples of heterocycloalkyl include, but are not limited to, 4-tetrahydropyranyl.

In the present invention, the term "heterocycloalkenyl" refers to a non-aromatic hydrocarbon ring system having one or more ring heteroatoms (e.g., N, O, S or Se) and one or more ring double bonds. Examples of heterocycloalkenyl include, but are not limited to, pyranyl.

In the present invention, the term "aryl" refers to an aromatic ring system, which may be a 6-carbon monocyclic, 10-carbon bicyclic, 14-carbon tricyclic aromatic ring system. Examples of aryl groups include, but are not limited to, phenyl, naphthyl, and anthracenyl.

In the present invention, the term "heteroaryl" refers to an aromatic ring system having one or more heteroatoms (such as O, N, S, or Se), which may be a 5-8 membered monocyclic, 8-12 membered bicyclic, or 11-14 membered tricyclic aromatic ring system having one or more heteroatoms. Examples of heteroaryl groups include, but are not limited to, pyridyl, furyl, imidazolyl, benzimidazolyl, pyrimidinyl, thienyl, quinolinyl, indolyl, and thiazolyl.

The above-mentioned alkyl, alkenyl, cycloalkyl, cycloalkenyl, heterocycloalkyl, heterocycloalkenyl, aryl and heteroaryl include both substituted and unsubstituted moieties. The term "substituted" refers to one or more substituents (which may be the same or different), each replacing a hydrogen atom. Examples of substituents include, but are not limited to, halogen (such as F, Cl, Br or I), hydroxyl, amino, alkylamino, arylamino, dialkylamino, diarylamino, cyano, nitro, mercapto, carbonyl, carbamido, carbamyl, carboxyl, thiocyanato, sulfoamido, alkyl, alkenyl, alkynyl, alkoxy, haloalkyl (i.e. alkyl substituted by one or more halogen atoms), aryl, heteroaryl, cyclyl, heterocyclyl, $CO_2$-alkyl and $CO_2$-alkenyl. Among these above-mentioned substituents, alkyl, alkenyl, alkoxy, aryl, heteroaryl, cyclyl, and heterocyclyl may be optionally further substituted with, for example, alkyl, alkenyl, alkoxy, haloalkyl, aryl, heteroaryl, halogen, hydroxyl, amino, mercapto, cyano, nitro, $CO_2$-alkyl or $CO_2$-alkenyl.

Regarding the amino alcohols represented in formula (I), $R_1$ is unsubstituted $C_{1-30}$ alkyl; $C_{1-30}$ alkyl substituted by one or more selected from the group consisting of halogen, cyano, $C_{1-30}$ alkoxy, $C_{1-30}$ haloalkyl, $C_{6-14}$ aryl, and 5-14 membered heteroaryl; —$CH_2$—$R_5$; or $R_6$. Wherein $R_5$ is selected from the group comprising unsubstituted $C_{3-15}$ cycloalkyl; $C_{3-15}$ cycloalkyl substituted by one or more selected from the group consisting of halogen, cyano, $C_{1-30}$ alkoxy, $C_{1-30}$ haloalkyl, $C_{6-14}$ aryl, and 5-14 membered heteroaryl; unsubstituted $C_{3-15}$ cycloalkenyl; $C_{3-15}$ cycloalkenyl substituted by one or more selected from the group consisting of halogen, cyano, $C_{1-30}$ alkoxy, $C_{1-30}$ haloalkyl, $C_{6-14}$ aryl, and 5-14 membered heteroaryl; unsubstituted $C_{3-15}$ hetrocycloalkyl; $C_{3-15}$ hetrocycloalkyl substituted by one or more selected from the group consisting of halogen, cyano, $C_{1-30}$ alkoxy, $C_{1-30}$ haloalkyl, $C_{6-14}$ aryl, and 5-14 membered heteroaryl; unsubstituted $C_{3-15}$ heterocycloalkenyl; and $C_{3-15}$ heterocycloalkenyl substituted by one or more selected from the group consisting of halogen, cyano, $C_{1-30}$ alkoxy, $C_{1-30}$ haloalkyl, $C_{6-14}$ aryl, and 5-14 membered heteroaryl R6 is selected from the group comprising unsubstituted $C_{3-15}$ cycloalkyl; $C_{3-15}$ cycloalkyl substituted by one or more selected from the group consisting of halogen, cyano, $C_{1-30}$ alkoxy, $C_{1-30}$ haloalkyl, $C_{6-14}$ aryl, and 5-14 membered heteroaryl; unsubstituted $C_{3-15}$ cycloalkenyl; $C_{3-15}$ cycloalkenyl substituted by one or more selected from the group consisting of halogen, cyano, $C_{1-30}$ alkoxy, $C_{1-30}$ haloalkyl, $C_{6-14}$ aryl, and 5-14 membered heteroaryl; unsubstituted $C_{3-15}$ hetrocycloalkyl; $C_{3-15}$ hetrocycloalkyl substituted by one or more selected from the group consisting of halogen, cyano, $C_{1-30}$ alkoxy, $C_{1-30}$ haloalkyl, $C_{6-14}$ aryl, and 5-14 membered heteroaryl; unsubstituted $C_{3-15}$ heterocycloalkenyl; $C_{3-15}$ heterocycloalkenyl substituted by one or more selected from the group consisting of halogen, cyano, $C_{1-30}$ alkoxy, $C_{1-30}$ haloalkyl, $C_{6-14}$ aryl, and 5-14 membered heteroaryl; unsubstituted $C_{6-14}$ aryl; $C_{6-14}$ aryl substituted by one or more selected from the group consisting of halogen, cyano, $C_{1-30}$ alkoxy, $C_{1-30}$ haloalkyl, $C_{6-14}$ aryl, and 5-14 membered heteroaryl; unsubstituted 5-14 membered hetreoaryl; and 5-14 membered hetreoaryl substituted by one or more selected from the group consisting of halogen, cyano, $C_{1-30}$ alkoxy, $C_{1-30}$ haloalkyl, $C_{6-14}$ aryl, and 5-14 membered heteroaryl.

Regarding the amino alcohols represented in formula (I), preferably, $R_1$ is unsubstituted $C_{1-10}$ alkyl; $C_{1-10}$ alkyl substituted by one or more selected from the group consisting of halogen, cyano, $C_{1-10}$ alkoxy, and $C_{1-10}$ haloalkyl; —$CH_2$—$R_5$; or $R_6$. Wherein $R_5$ and $R_6$ are selected from the group comprising unsubstituted $C_{3-15}$ cycloalkyl; $C_{3-15}$ cycloalkyl substituted by one or more selected from the group consisting of halogen, cyano, $C_{1-10}$ alkoxy, $C_{1-10}$ haloalkyl, $C_{6-14}$ aryl, and 5-14 membered heteroaryl; unsubstituted $C_{3-15}$ cycloalkenyl; $C_{3-15}$ cycloalkenyl substituted by one or more selected from the group consisting of halogen, cyano, $C_{1-10}$ alkoxy, $C_{1-10}$ haloalkyl, $C_{6-14}$ aryl, and 5-14 membered heteroaryl; unsubstituted $C_{3-15}$ hetrocycloalkyl; $C_{3-15}$ hetrocycloalkyl substituted by one or more selected from the group consisting of halogen, cyano, $C_{1-10}$ alkoxy, $C_{1-10}$ haloalkyl, $C_{6-14}$ aryl, and 5-14 membered heteroaryl; unsubstituted $C_{3-15}$ heterocycloalkenyl; $C_{3-15}$ heterocycloalkenyl substituted by one or more selected from the group consisting of halogen, cyano, $C_{1-10}$ alkoxy, $C_{1-10}$ haloalkyl, $C_{6-14}$ aryl, and 5-14 membered heteroaryl; unsubstituted $C_{6-14}$ aryl; $C_{6-14}$ aryl substituted by one or more selected from the group consisting of halogen, cyano, $C_{1-10}$ alkoxy, $C_{1-10}$ haloalkyl, $C_{6-14}$ aryl, and 5-14 membered heteroaryl; unsubstituted 5-14 membered hetreoaryl; and 5-14 membered hetreoaryl substituted by one or more selected from the group consisting of halogen, cyano, $C_{1-10}$ alkoxy, $C_{1-10}$ haloalkyl, $C_{6-14}$ aryl, and 5-14 membered heteroaryl.

Regarding the amino alcohols represented in formula (I), more preferably, $R_1$ is unsubstituted $C_{1-10}$ alkyl; $C_{1-10}$ alkyl substituted by one or more selected from the group consisting of halogen, cyano, $C_{1-10}$ alkoxy, $C_{1-10}$ haloalkyl; —$CH_2$—$R_5$; or $R_6$. Wherein $R_5$ and $R_6$ are selected from the group comprising unsubstituted $C_{6-14}$ aryl; $C_{6-14}$ aryl substituted by one or more selected from the group consisting of halogen, cyano, $C_{1-10}$ alkoxy, $C_{1-10}$ haloalkyl, $C_{6-14}$ aryl, and 5-14 membered heteroaryl; unsubstituted 5-14 membered hetreoaryl; and 5-14 membered hetreoaryl substituted by one or more selected from the group consisting of halogen, cyano, $C_{1-10}$ alkoxy, $C_{1-10}$ haloalkyl, $C_{6-14}$ aryl, and 5-14 membered heteroaryl.

Specifically, the amino alcohols represented in formula (I) includes:

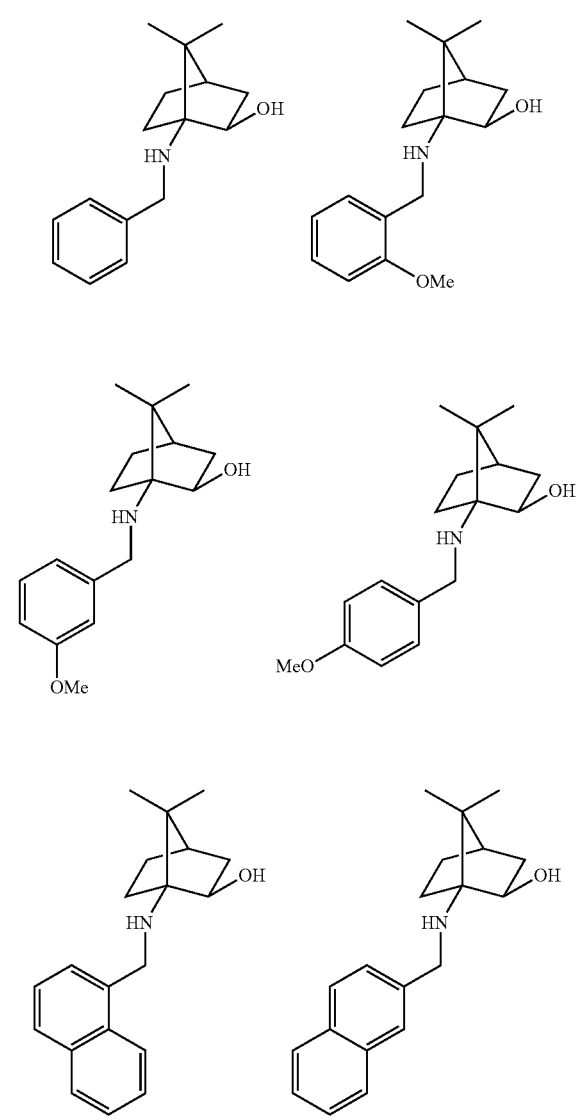

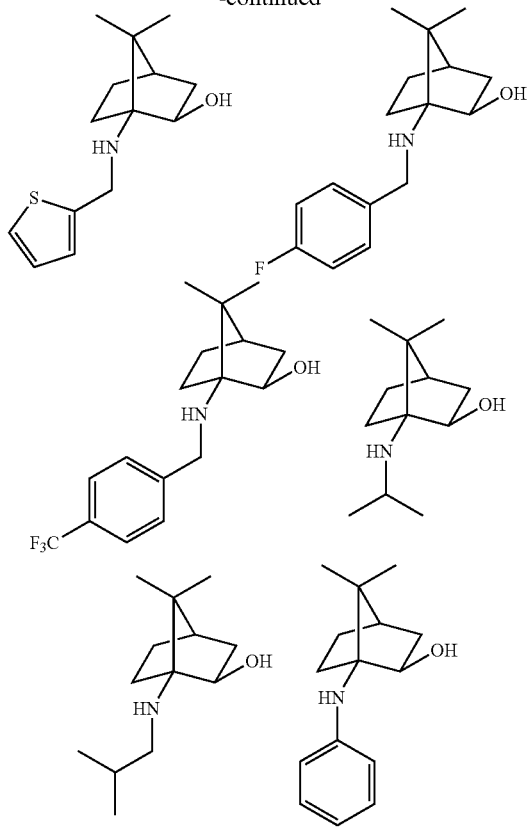

Regarding $R_2CH=NY$, preferably, $R_2$ is unsubstituted or substituted $C_{1-30}$ alkyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; $(CH_2)_iR_a$; unsubstituted or substituted $C_{2-30}$ alkenyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; $(CH_2)_rCH=CH(CH_2)_kR_a$; unsubstituted or substituted $C_{5-14}$ cycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $R_a$ is substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; i is an integer of 1 to 30; and each of r and k independently is an integer of 0 to 30.

Regarding $R_2CH=NY$, more preferably, $R_2$ is unsubstituted or substituted $C_{1-10}$ alkyl by one or more selected from the group consisting of $C_{6-14}$ aryl and 5-14 membered heteroaryl; $(CH_2)_iR_a$; unsubstituted or substituted $C_{2-10}$ alkenyl by one or more selected from the group consisting of $C_{6-14}$ aryl and 5-14 membered heteroaryl; $(CH_2)_rCH=CH(CH_2)_k$ $R_a$; unsubstituted $C_{5-14}$ cycloalkyl; unsubstituted $C_{5-14}$ cycloalkenyl; unsubstituted or substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or unsubstituted or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl, and $CO_2$—$C_{2-10}$ alkenyl; $R_a$ is substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl, and $CO_2$—$C_{2-10}$ alkenyl; or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl, and $CO_2$—$C_{2-10}$ alkenyl; i is an integer of 1 to 10; and each of r and k independently is an integer of 0 to 10.

Regarding $R_2CH=NY$, most preferably, $R_2$ is unsubstituted $C_{1-10}$ alkyl (e.g. $(CH_2)_{0-9}CH_3$); substituted $C_{1-10}$ alkyl by phenyl or naphthyl (e.g. $CH_2CH_2C_6H_5$ or $CH_2CH_2C_{10}H_7$); unsubstituted $C_{2-10}$ alkenyl (e.g. $(CH_2)_{0-8}$ $CH=CH$); substituted $C_{2-10}$ alkenyl by phenyl or naphthyl (e.g. $CH=CHC_6H_5$, $CH=CHC_{10}H_7$, $CH_2CH=CHC_6H_5$ or $CH_2CH=CHC_{10}H_7$); unsubstituted $C_{5-10}$ cycloalkyl (e.g. cyclohexyl); unsubstituted $C_{5-10}$ cycloalkenyl; unsubstituted phenyl or naphthyl; substituted phenyl or naphthyl by one or more selected from the group consisting of halogen, cyano, $C_{1-10}$ alkyl (e.g. $(CH_2)_{0-9}CH_3$), $C_{2-10}$ alkenyl (e.g. $(CH_2)_{0-8}$ $CH=CH_2$), $C_{1-10}$ alkoxy (e.g. $O(CH_2)_{0-9}CH_3$), $C_{1-10}$ haloalkyl (e.g. $(CH_2)_{0-9}CF_3$, $(CH_2)_{0-9}CCl_3$, $(CH_2)_{0-9}CBR2$), $CO_2$—$C_{1-10}$ alkyl (e.g. $CO_2(CH_2)_{0-9}CH_3$) and $CO_2$—$C_{2-10}$ alkenyl (e.g. $CO_2(CH_2)_{0-7}CH=CH_2$), in which a substitute on phenyl is preferably at meta- or para-position; $(CH_2)_iR_a$; or $(CH_2)_rCH=CH(CH_2)_kR_a$, in which $R_a$ is substituted phenyl or naphthyl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; i is an integer of 1 to 10; and each of r and k independently is an integer of 0 to 8, and the sum of r and k is 8 (e.g. $CH_2CH_2C_6H_4CH_3$, $CH_2CH_2C_{10}H_6CH_3$, $CH=CHC_6H_4CH_3$, $CH=CHC_{10}H_6CH_3$, $CH_2CH=CHC_6H_4CH_3$ or $CH_2CH=CHC_{10}H_6CH_3$).

Examples of $R_2CH=NY$ include, but are not limited to:

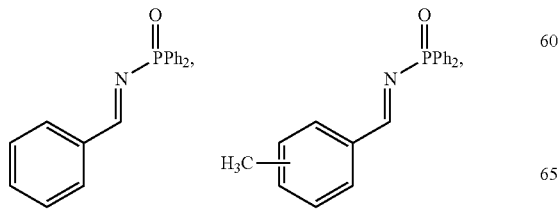

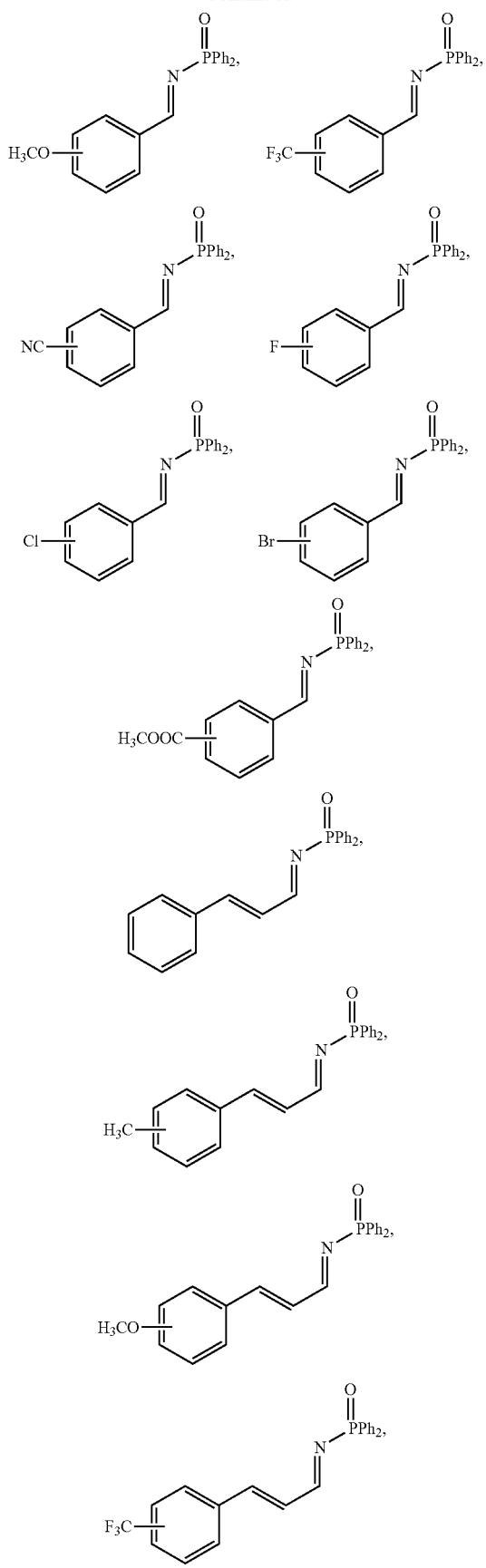

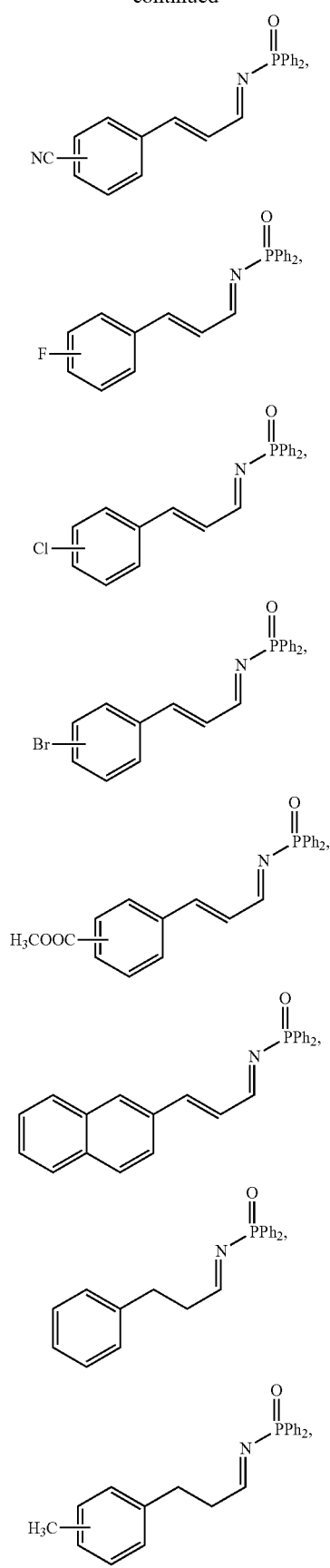
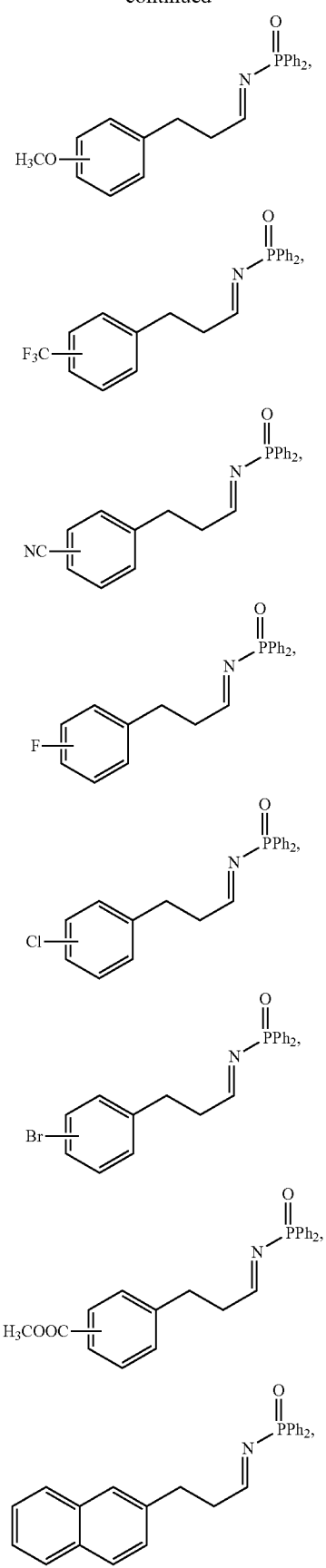

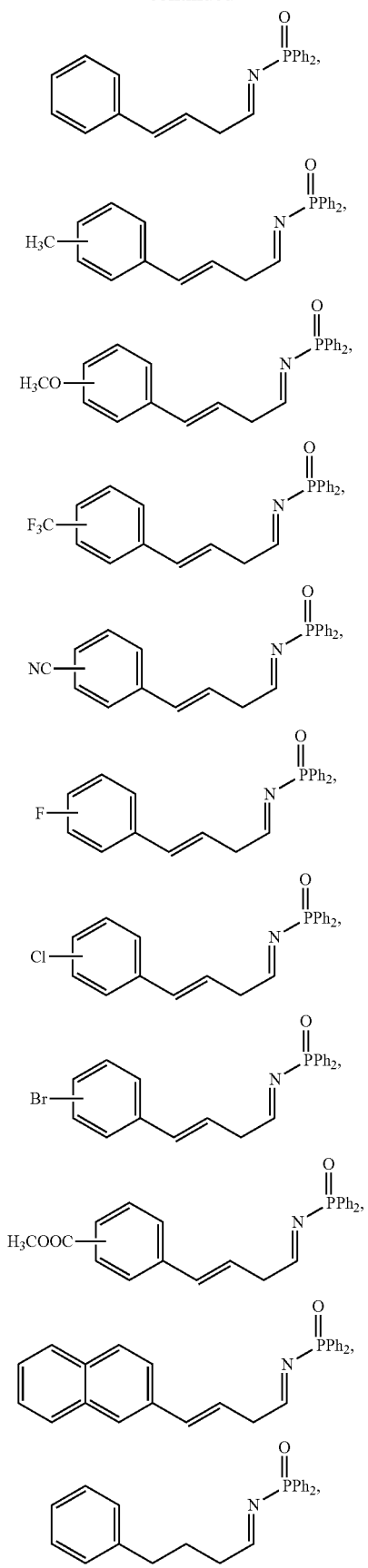
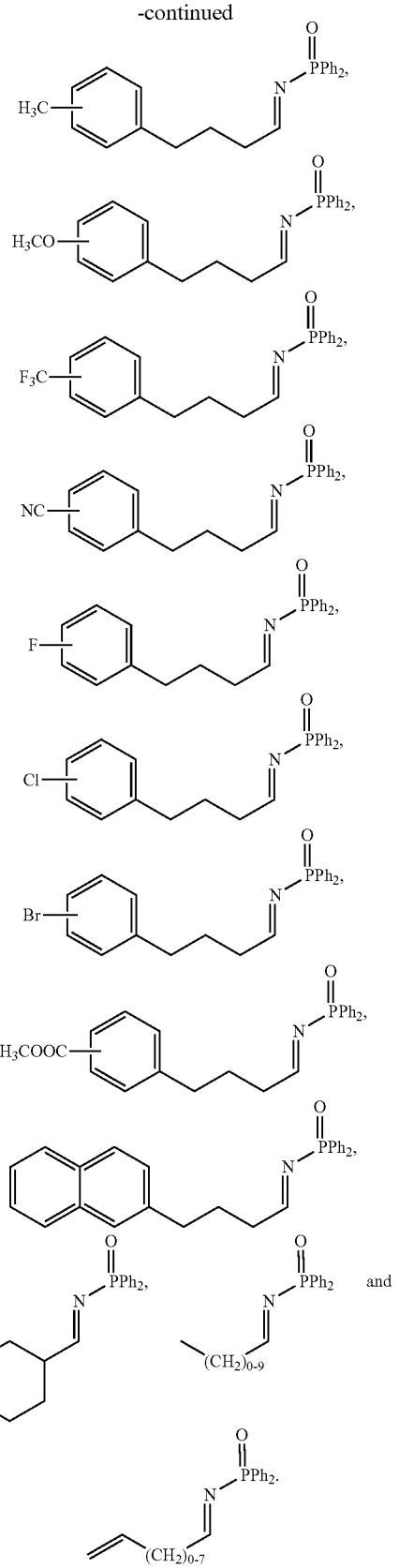
Regarding $R_3ZnR_4$, preferably, each of $R_3$ and $R_4$ independently is unsubstituted or substituted $C_{1-30}$ alkyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; unsubstituted or substituted $C_{2-30}$ alkenyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and $C_{5-14}$ heteroaryl; unsubstituted or substituted $C_{5-14}$ cycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl.

Regarding $R_3ZnR_4$, more preferably, $R_3$ is unsubstituted $C_{1-10}$ alkyl; and $R_4$ is unsubstituted or substituted $C_{1-10}$ alkyl by one or more selected from the group consisting of 5-14 membered heteroaryl and $C_{6-14}$ aryl; unsubstituted or substituted $C_{2-10}$ alkenyl by one or more selected from the group consisting of $C_{6-14}$ aryl and 5-14 membered heteroaryl; unsubstituted $C_{5-14}$ cycloalkyl; unsubstituted $C_{5-14}$ cycloalkenyl; unsubstituted or substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl.

Regarding $R_3ZnR_4$, most preferably, $R_3$ is unsubstituted $C_{1-10}$ alkyl (e.g. $(CH_2)_{0-9}CH_3$); and R4 is unsubstituted $C_{1-10}$ alkyl (e.g. $(CH_2)_{0-9}CH_3$); unsubstituted $C_{2-10}$ alkenyl (e.g. $C(C_2H_5)=CH(C_2H_5)$, $CH=CHC(CH_3)_3$, $CH=CH(CH_2)_{0-7}CH_3$); substituted $C_{2-10}$ alkenyl by phenyl or naphthyl (e.g. $CH=CH(CH_2)_{0-8}C_6H_5$, $CH=CH(CH_2)_{0-8}C_{10}H_7$); unsubstituted phenyl or naphthyl; or substituted phenyl or naphthyl by one or more selected from the group consisting of halogen, cyano, $C_{1-10}$ alkyl (e.g. $(CH_2)_{0-9}CH_3$), $C_{2-10}$ alkenyl (e.g. $(CH_2)_{0-8}CH=CH_2$), $C_{1-10}$ alkoxy (e.g. $O(CH_2)_{0-9}CH_3$), $C_{1-10}$ haloalkyl (e.g. $(CH_2)_{0-9}CF_3$, $(CH_2)_{0-9}CCl_3$, $(CH_2)_{0-9}CBR2$), $CO_2$—$C_{1-10}$ alkyl (e.g. $CO_2(CH_2)_{0-9}CH_3$) and $CO_2$—$C_{2-10}$ alkenyl (e.g. $CO_2(CH_2)_{0-8}CH=CH_2$).

Examples of $R_3ZnR_4$ include, but not limited to, $Zn(CH_3)_2$,

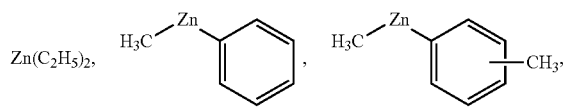

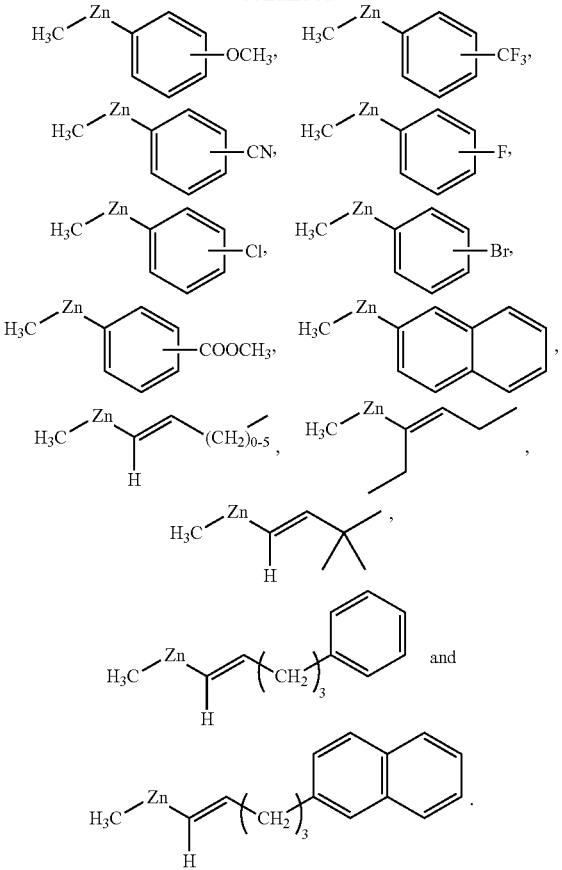

In the method of enantioselective addition according to the present invention, the compound represented by the formula (I) may be used in an amount from 0.01 to 1 equivent, preferably from 0.05 to 0.6 equivent, more preferably from 0.05 to 0.6 equivent, and most preferably from 0.05 to 0.3 equivent based on $R_2CH=NY$.

In the method of enantioselective addition according to the present invention, $R_2CH=NY$ may be reacted with $R_3ZnR_4$ at a temperature in a range from 0° C. to 50° C., and preferably from 0° C. to 25° C.

In the method of enantioselective addition according to the present invention, $R_3ZnR_4$ may be used in an amount from 1 to 10 equivents, preferably from 2 to 6 equivents, and more preferably from 3 to 6 equivents based on $R_2CH=NY$.

In the method of enantioselective addition according to the present invention, $R_2CH=NY$ may be reacted with $R_3ZnR_4$ in a solvent, and preferably in an aprotic solvent. Herein, the aprotic solvent may be selected from the group consisting of n-hexane, toluene, dichloromethane, tetrahydrofuran, acetonitrile, a mixture of n-haxane and toluene, a mixture of n-haxane and dichloromethane, a mixture of n-hexane and tetrahydrofuran, and a mixture of n-haxane and acetonitrile. Preferably, the aprotic solvent may be selected from the group consisting of n-hexane, toluene, a mixture of n-hexane and toluene in a ratio of 1:1 to 1:5, a mixture of n-hexane and dichloromethane in a ratio of 1:1 to 1:3, a mixture of n-hexane and tetrahydrofuran in a ratio of 1:1 to 1:3, and a mixture of n-hexane and acetonitrile in a ratio of 1:1 to 1:3.

In the method of enantioselective addition according to the present invention, the concentration of $R_2CH=NY$ in the aprotic solvent may range from 0.01 M to 1 M, preferably from 0.057 M to 0.6 M, and more preferably from 0.057 M to 0.55 M.

In the method of enantioselective addition according to the present invention, further comprises a step of: adding an accelerator, wherein the accelerator is at least one selected from the group consisting of methanol, ethanol, isopropanol, water, triisopropylchlorosilane (TIPSCl), trimethyl borate, and triphenylphosphine oxide. Preferably, the accelerator is at least one selected from the group consisting of methanol, trimethyl borate, and triphenylphosphine oxide. More preferably, the accelerator is methanol. In addition, the accelerator may be used in an amount from 0.1 to 3 equivent; preferably, from 0.2 to 2.5 equivent based on $R_2CH=NY$.

Accordingly, the present invention uses the above-mentioned compound represented by the formula (I) to perform enantioselective addition of organozincs to imines, so as to prepare secondary amines in high yield and enantiomeric excess (ee).

DETAILED DESCRIPTION OF THE PREFERRED EMBODIMENT

Synthesis of N-mono-substituted β-amino Alcohols (3a-k)

Reaction scheme 1:

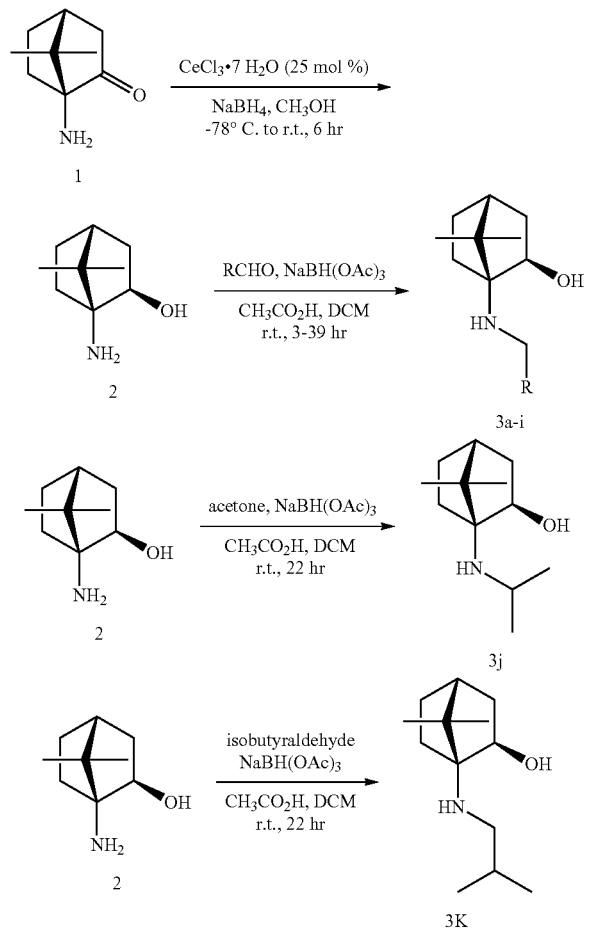

3a. R = Ph 3b. R = 2-MeOC$_6$H$_4$ 3c. R = 3-MeOC$_6$H$_4$ 3d. R = 4-MeOC$_6$H$_4$ 3e. R = 1-naphthyl 3f. R = 2-naphthyl 3g. R = 2-thienyl 3h. R = 4-FC$_6$H$_4$ 3i. R = 4-F$_3$CC$_6$H$_4$ According to the reaction scheme 1, the starting material of the preparation reaction is (1S,4R)-1-amino-7,7-Dimethyl-bicyclo[2.2.1]heptan-2-one (compound 1), and the N-mono-substituted β-amino alcohols 3a-k were synthesized in two steps (Scheme 1).

PREPARATION EXAMPLE 1

Synthesis of (1S,2R,4R)-1-amino-2-exo-hydroxy-7,7-Dimethyl-bicyclo[2.2.1]heptane (Compound 2)

To a solution of (1S,4R)-1-amino-7,7-Dimethyl-bicyclo[2.2.1]heptan-2-one (compound 1) (4.0 g, 26.1 mmol) and CeCl$_3$·7H$_2$O (2.4 g, 6.5 mmol) in methanol (0.20 M, 130.6 mL) at −78° C. was added NaBH$_4$ (4.6 g, 121.5 mmol). The temperature was raised to room temperature (25-28° C.). The reaction mixture was stirred for 6 h and then removed the methanol. Water (80 mL) was added and the aqueous phase was extracted with dichloromethane (60 mL×3). The combined organic extracts were washed with brine and dried over anhydrous sodium sulfate. Filtration and evaporated afforded a residue that was purified by column chromatography with methanol/EA (1/5) as eluent to give white solid (3.03 g, 75%). Mp: 246.3-247.7° C.; $[\alpha]_D^{24.8}$ −2.35 (c 1.0, CHCl$_3$); $^1$H NMR (400 MHz, CDCl$_3$) δ3.64 (dd, J=6.0, 5.6 Hz, 1H), 1.76-1.68 (m, 4H), 1.53-1.45 (m, 1H), 1.14-1.05 (m, 2H), 0.96 (s, 3H), 0.79 (s, 3H); $^{13}$C NMR (100 MHz, CDCl$_3$) δ 76.3 (CH), 64.6 (C), 45.4 (C), 42.2 (CH), 38.8 (CH$_2$), 32.4 (CH$_2$), 26.4 (CH$_2$), 19.5 (CH$_3$), 19.1 (CH$_3$); IR: (neat) 3516, 3458, 2945, 1562, 1076 cm$^{-1}$; HRMS (EI) Calculated for C$_9$H$_{17}$NO: 155.1310. Found: 155.1312.

PREPARATION EXAMPLE 2

Synthesis of (1S,2R,4R)-N-aryl-1-amino-2-exo-hydroxy-7,7-dimethyl-bicyclo[2.2.1]heptane (Compounds 3a-3i)

A solution of (1S,2R,4R)-1-amino-2-exo-hydroxy-7,7-Dimethyl-bicyclo[2.2.1]heptane (compound 2) and aryl aldehyde (1.1 equiv.) in anhydrous dichloromethane, then added sodium triacetoxyborohydride (1.4 equiv.) and acetic acid (1.1 equiv.). The reaction mixture was stirred 3-39 hr at room temperature (25-28° C.), and quenched with aqueous NaOH. The aqueous phase was extracted with dichloromethane, and the combined organic layer was washed with brine three times. The organic layer was dried over anhydrous sodium sulfate and evaporated to dryness under reduced pressure. Purification of the crude product on silica chromatography with EA/Hexanes (1/5) gave 3a-3i.

PREPARATION EXAMPLE 2-1

Synthesis of (1S,2R,4R)-N-benzyl-1-amino-2-exo-hydroxy-7,7-dimethyl-bicyclo[2.2.1]heptane (Compound 3a)

According to the synthesis method of preparation example 2, the procedure was followed by using compound 2 (1.0 g, 6.4 mmol), benzaldehyde (7.0 mmol), anhydrous dichloromethane (0.26 M, 25.0 ml), sodium triacetoxyborohydride (9.0 mmol), and acetic acid (7.0 mmol). The reaction was worked up after 3 hr and purified by column chromatography on silica gel (EtOAc:hexanes=1:5 as eluant) to obtain compound 3a as a white solid (1.3 g) in 86% yield. Mp: 69.6-70.6° C.; $[\alpha]_D^{20.7}$ −2.97 (c 1.0, CHCl$_3$); $^1$H NMR (400 MHz, CDCl$_3$) δ 7.36-7.30 (m, 4H), 7.27-7.23 (m, 1H), 3.75-3.66 (m, 3H), 3.33 (br, 1H), 1.94-1.68 (m, 5H), 1.39-1.33 (m, 1H), 1.23-1.15 (m, 1H), 1.02 (s, 3H), 0.88 (s, 3H); $^{13}$C NMR (100

MHz, CDCl$_3$) δ 140.7 (C), 128.4 (CH), 128.0 (CH), 127.0 (CH), 72.7 (CH), 68.5 (C), 48.4 (CH$_2$), 46.6 (C), 43.1 (CH), 39.4 (CH$_2$), 29.4 (CH$_2$), 27.0 (CH$_2$), 20.3 (CH$_3$), 19.9 (CH$_3$); IR (neat) 3317, 3260, 2958, 2942, 2875, 2834, 1453, 1078, 728, 700 cm$^{-1}$; HRMS (EI) Calculated for C$_{16}$H$_{23}$NO: 245.1780. Found: 245.1782.

PREPARATION EXAMPLE 2-2

Synthesis of (1S,2R,4R)-N-2'-methoxylbenzyl-1-amino-2-exo-hydroxy-7,7-dimethyl-bicyclo[2.2.1]heptane (Compound 3b)

According to the synthesis method of preparation example 2, the procedure was followed by using compound 2 (0.5 g, 3.2 mmol), 2-methoxybenzaldehyde (3.5 mmol), anhydrous dichloromethane (0.21 M, 15.0 ml), sodium triacetoxyborohydride (4.5 mmol), acetic acid (3.5 mmol). The reaction was worked up after 17 hr and purified by column chromatography on silica gel (EtOAc:hexanes=1:5 as eluant) to afford compound 3b as a viscid liquid (0.7 g) in 80% yield. $[\alpha]_D^{21.1}$−6.28 (c 1.0, CHCl$_3$); $^1$H NMR (400 MHz, CDCl$_3$) δ 7.27-7.23 (m, 2H), 6.93-6.86 (m, 2H), 3.86-3.83 (m, 1H), 3.84 (s, 3H), 3.68 (s, 2H), 1.90-1.66 (m, 5H), 1.39-1.32 (m, 1H), 1.19-1.14 (m, 1H), 1.00 (s, 3H), 0.86 (s, 3H); $^{13}$C NMR (100 MHz, CDCl$_3$) δ 157.4 (C), 130.0 (CH), 128.7 (C), 128.5 (CH), 120.6 (CH), 110.3 (CH), 72.7 (CH), 68.5 (C), 55.2 (CH$_3$), 46.4 (C), 44.2 (CH$_2$), 43.1 (CH), 38.9 (CH$_2$), 29.3 (CH$_2$), 27.1 (CH$_2$), 20.3 (CH$_3$), 19.8 (CH$_3$); IR (neat) 3444, 2953, 2879, 1603, 1589, 1494, 1463, 1455, 1242, 1028, 753 cm$^{-1}$; HRMS (EI) Calculated for C$_{17}$H$_{25}$NO$_2$: 275.1885. Found: 275.1878.

PREPARATION EXAMPLE 2-3

Synthesis of (1S,2R,4R)-N-3'-methoxylbenzyl-1-amino-2-exo-hydroxy-7,7-dimethyl-bicyclo[2.2.1]heptane (Compound 3c)

According to the synthesis method of preparation example 2, the procedure was followed by using compound 2 (0.5 g, 3.2 mmol), 3-methoxybenzaldehyde (3.5 mmol), anhydrous dichloromethane (0.21 M, 15.0 ml), sodium triacetoxyborohydride (4.5 mmol), acetic acid (3.5 mmol). The reaction was worked up after 17 hr and purified by column chromatography on silica gel (EtOAc:hexanes=1:5 as eluant) to afford compound 3c as a white solid (0.7 g) in 87% yield. Mp 66.7-67.6° C.; $[\alpha]_D^{22.0}$−1.88 (c 1.0, CHCl$_3$); $^1$H NMR (400 MHz, CDCl$_3$) δ 7.25-7.21 (m, 1H), 6.93-6.90 (m, 2H), 6.79 (dd, J=8.0, 2.4 Hz, 1H), 3.79 (s, 3H), 3.74-3.64 (m, 3H), 3.30 (br, 1H), 1.93-1.68 (m, 5H), 3.30 (br, 1H), 1.38-1.32 (m, 1H), 1.25-1.14 (m, 1H), 1.02 (s, 3H), 0.88 (s, 3H); $^{13}$C NMR (100 MHz, CDCl$_3$) δ 159.7 (C), 142.5 (C), 129.4 (CH), 120.3 (CH), 113.7 (CH), 112.3 (CH), 72.7 (CH), 68.5 (C), 55.2 (CH$_3$), 48.4 (CH$_2$), 46.6 (C), 43.2 (CH), 39.4 (CH$_2$), 29.4 (CH$_2$), 27.0 (CH$_2$), 20.3 (CH$_3$), 19.9 (CH$_3$); IR (neat) 3409, 2953, 2879, 1602, 1585, 1455, 1263, 751, 690 cm$^{-1}$; HRMS (EI) Calculated for C$_{17}$H$_{25}$NO$_2$: 275.1885. Found: 275.1879.

PREPARATION EXAMPLE 2-4

Synthesis of (1S,2R,4R)-N-4'-methoxylbenzyl-1-amino-2-exo-hydroxy-7,7-dimethyl-bicyclo[2.2.1]heptane (Compound 3d)

According to the synthesis method of preparation example 2, the procedure was followed by using compound 2(0.5 g, 3.2 mmol), 4-methoxybenzaldehyde (3.5 mmol), anhydrous dichloromethane (0.21 M, 15.0 ml), sodium triacetoxyborohydride (4.5 mmol), acetic acid (3.5 mmol). The reaction was worked up after 39 hr and purified by column chromatography on silica gel (EtOAc:hexanes=1:5 as eluant) to afford compound 3d as a white solid (0.6 g) in 73% yield. Mp 45.3-46.2° C.; $[\alpha]_D^{22.7}$−5.18 (c 1.0, CHCl$_3$); $^1$H NMR (400 MHz, CDCl$_3$) δ 7.27-7.24 (m, 2H), 6.87-6.83 (m, 2H), 3.78 (s, 3H), 3.71 (dd, J=8.0, 3.2 Hz, 1H), 3.67 (d, J=12.4 Hz, 1H), 3.60 (d, J=12.4 Hz, 1H), 3.37 (br, 1H), 1.93-1.67 (m, 5H), 1.38-1.32 (m, 1H), 1.20-1.14 (m, 1H), 1.00 (s, 3H), 0.87 (s, 3H); $^{13}$C NMR (100 MHz, CDCl$_3$) δ 158.7 (C), 132.9 (C), 129.2 (CH), 113.8 (CH), 72.7 (CH), 68.4 (C), 55.2 (CH), 47.8 (CH$_2$), 46.6 (C), 43.2 (CH), 39.4 (CH$_2$), 29.3 (CH$_2$), 27.0 (CH$_2$), 20.3 (CH$_3$), 19.9 (CH$_3$); IR (neat) 3409, 2953, 1611, 1513, 1247, 821 cm$^{-1}$; HRMS (EI) Calculated for C$_{17}$H$_{25}$NO$_2$: 275.1885. Found: 275.1877.

PREPARATION EXAMPLE 2-5

Synthesis of (1S,2R,4R)-N-(1-naphthylmethyl)-1-amino-2-exo-hydroxy-7,7-dimethyl-bicyclo[2.2.1]heptane (Compound 3 e)

According to the synthesis method of preparation example 2, the procedure was followed by using compound 2 (0.5 g, 3.2 mmol), 1-naphthaldehyde (3.5 mmol), anhydrous dichloromethane (0.21 M, 15.0 ml), sodium triacetoxyborohydride (4.5 mmol), acetic acid (3.5 mmol). The reaction was worked up after 14 hr and purified by column chromatography on silica gel (EtOAc:hexanes=1:5 as eluant) to afford compound 3e as a white solid (0.8 g) in 85% yield. Mp 71.9-72.9° C.; $[\alpha]_D^{23.4}$+0.76 (c 1.0, CHCl$_3$); $^1$H NMR (400 MHz, CDCl$_3$) δ 8.11 (d, J=8.4 Hz, 1H), 7.87-7.84 (m, 1H), 7.77 (d, J=8.0 Hz, 1H), 7.55-7.41 (m, 4H), 4.24 (d, J=12.4 Hz, 1H), 4.10 (d, J=12.4 Hz, 1H), 3.85 (dd, J=7.6, 3.2 Hz, 1H), 3.29 (br, 1H), 1.95-1.71 (m, 5H), 1.55-1.48 (m, 1H), 1.38 (br, 1H), 1.28-1.21 (m, 1H), 1.00 (s, 3H), 0.91 (s, 3H); $^{13}$C NMR (100 MHz, CDCl$_3$) δ 136.4 (C), 133.8 (C), 131.6 (C), 128.7 (CH), 127.8 (CH), 126.2 (CH), 126.0 (CH), 125.6 (CH), 125.4 (CH), 123.4 (CH), 73.0 (CH), 68.7 (C), 46.7 (C), 45.9 (CH$_2$), 43.2 (CH), 39.6 (CH$_2$), 29.3 (CH$_2$), 27.1 (CH$_2$), 20.3(CH$_3$), 19.9 (CH$_3$); IR (neat) 3409, 2952, 2870, 1453, 1073, 791, 778 cm$^{-1}$; HRMS (EI) Calculated for C$_{20}$H$_{25}$NO: 295.1936. Found: 295.1927.

PREPARATION EXAMPLE 2-6

Synthesis of (1S,2R,4R)-N-(2-naphthylmethyl)-1-amino-2-exo-hydroxy-7,7-dimethyl-bicyclo[2.2.1]heptane (Compound 3f)

According to the synthesis method of preparation example 2, the procedure was followed by using compound 2 (0.5 g, 3.2 mmol), 2-naphthaldehyde (3.5 mmol), anhydrous dichloromethane (0.21 M, 15.0 ml), sodium triacetoxyborohydride (4.5 mmol), acetic acid (3.5 mmol). The reaction was worked up after 13 hr and purified by column chromatography on silica gel (EtOAc:hexanes=1:5 as eluant) to afford compound 3f as a white solid (0.7 g) in 76% yield. Mp 64.2-65.2° C.; $[\alpha]_D^{23.4}$+5.24 (c 1.0, CHCl$_3$); $^1$H NMR (400 MHz, CDCl$_3$) δ 7.81-7.80 (m, 4H), 7.49-7.41 (m, 3H), 3.90 (d, J=12.8 Hz, 1H), 3.84 (d, J=12.8 Hz, 1H), 3.77 (dd, J=7.6, 3.2 Hz, 1H), 3.37 (br, 1H), 1.96-1.70 (m, 5H), 1.43-1.38 (m, 1H), 1.23-1.17 (m, 1H), 1.04 (s, 3H), 0.91 (s, 3H); $^{13}$C NMR (100 MHz, CDCl$_3$) δ 138.2 (C), 133.3 (C), 132.6 (C), 128.0 (CH), 127.6 (CH×2), 126.5 (CH), 126.2 (CH), 126.0 (CH), 125.5 (CH), 72.8 (CH), 68.5 (C), 48.5 (CH$_2$), 46.6 (C), 43.1 (CH), 39.4

(CH$_2$), 29.4 (CH$_2$), 27.0 (CH$_2$), 20.3 (CH$_3$), 19.9 (CH$_3$); IR (neat) 3409, 2952, 2878, 1454, 1080, 812, 743 cm$^{-1}$; HRMS (EI) Calculated for C$_{20}$H$_{25}$NO: 295.1936. Found: 295.193.

PREPARATION EXAMPLE 2-7

Synthesis of (1S,2R,4R)-N-(2-thienylmethyl)-1-amino-2-exo-hydroxy-7,7-dimethyl-bicyclo[2.2.1]heptane (Compound 3g)

According to the synthesis method of preparation example 2, the procedure was followed by using compound 2 (0.36 g, 2.3 mmol), 2-thiophenecarboxaldehyde (2.5 mmol), anhydrous dichloromethane (0.23 M, 10.0 ml), sodium triacetoxyborohydride (3.2 mmol), acetic acid (2.5 mmol). The reaction was worked up after 39 hr and purified by column chromatography on silica gel (EtOAc:hexanes=1:5 as eluant) to afford compound 3g as a white solid (0.3 g) in 51% yield. Mp 58.2-59.2° C.; [α]$_D^{23.6}$–15.67 (c 1.0, CHCl$_3$); $^1$H NMR (400 MHz, CDCl$_3$) δ 7.20-7.18 (m, 1H), 6.94-6.93 (m, 2H), 4.00 (d, J=13.6 Hz, 1H), 3.85 (d, J=13.6 Hz, 1H), 3.72 (dd, J=7.6, 3.2 Hz, 1H), 3.19 (br, 1H), 1.94-1.68 (m, 5H), 1.45 (br, 1H), 1.36-1.29 (m, 1H), 1.20-1.14 (m, 1H), 1.03 (s, 3H), 0.89 (s, 3H); $^{13}$C NMR (100 MHz, CDCl$_3$) δ 144.7 (C), 126.5 (CH), 124.3 (CH), 124.2 (CH), 72.8 (CH), 68.4 (C), 46.6 (C), 43.2 (CH$_2$), 43.0 (CH), 39.4 (CH$_2$), 29.2 (CH$_2$), 26.9 (CH$_2$), 20.3 (CH$_3$), 19.8 (CH$_3$); IR (neat) 3409, 2953, 2879, 1455, 1079, 850, 694 cm$^{-1}$; HRMS (EI) Calculated for C$_{14}$H$_{2i}$NOS: 251.1344. Found: 251.1338.

PREPARATION EXAMPLE 2-8

Synthesis of (1S,2R,4R)-N-4'-fluorobenzyl-1-amino-2-exo-hydroxy-7,7-dimethyl-bicyclo[2.2.1]heptane (Compound 3h)

According to the synthesis method of preparation example 2, the procedure was followed by using compound 2 (0.5 g, 3.2 mmol), 4-fluorobenzaldehyde (3.5 mmol), anhydrous dichloromethane (0.21 M, 15.0 ml), sodium triacetoxyborohydride (4.5 mmol), acetic acid (3.5 mmol). The reaction was worked up after 32 hr and purified by column chromatography on silica gel (EtOAc:hexanes=1:5 as eluant) to afford compound 3 h as a white solid (0.55 g) in 65% yield. Mp 59.3-60.2° C.; [α]$_D^{23.4}$–2.14 (c 1.0, CHCl$_3$); $^1$H NMR (400 MHz, CDCl$_3$) δ 7.32-7.28 (m, 2H), 7.02-6.96 (m, 2H), 3.73 (dd, J=7.6, 3.2 Hz, 1H), 3.70 (d, J=12.8 Hz, 1H), 3.64 (d, J=12.8 Hz, 1H), 3.26 (br, 1H), 1.94-1.68 (m, 5H), 1.37-1.31 (m, 1H), 1.20-1.14 (m, 1H), 1.02 (s, 3H), 0.88 (s, 3H); $^{13}$C NMR (100 MHz, CDCl$_3$) δ 161.9 (d, J=243.2 Hz, C), 136.4 (C), 129.5 (d, J=8.4 Hz, CH), 115.7 (d, J=21.2 Hz, CH), 72.7 (CH), 68.4 (C), 47.6 (CH$_2$), 46.6 (C), 43.1 (CH), 39.5 (CH$_2$), 29.3 (CH$_2$), 27.0 (CH$_2$), 20.3(CH$_3$), 19.9 (CH$_3$); IR (neat) 3369, 2954, 2879, 1509, 1221, 1079, 822 cm$^{-1}$; HRMS (EI) Calculated for C$_{16}$H$_{22}$FNO: 263.1685. Found: 263.1683.

PREPARATION EXAMPLE 2-9

Synthesis of (1S,2R,4R)-N-4'-trifluoromethylbenzyl-1-amino-2-exo-hydroxy-7,7-dimethyl-bicyclo[2.2.1]heptane (compound 3i)

According to the synthesis method of preparation example 2, the procedure was followed by using compound 2 (0.5 g, 3.2 mmol), 4-(trifluoromethyl)benzaldehyde (3.5 mmol), anhydrous dichloromethane (0.21 M, 15.0 ml), sodium triacetoxyborohydride (4.5 mmol), acetic acid (3.5 mmol). The reaction was worked up after 32 hr and purified by column chromatography on silica gel (EtOAc:hexanes=1:5 as eluant) to afford compound 3i as a white solid (0.7 g) in 72% yield. Mp 33.0-34.0° C.; [α]$_D^{23.9}$–5.09 (c 1.0, CHCl$_3$); $^1$H NMR (400 MHz, CDCl$_3$) δ 7.56 (d, J=8.0 Hz, 2H), 7.46 (d, J=8.0 Hz, 2H), 3.81-3.74 (m, 3H), 3.15 (br, 1H), 1.94-1.68 (m, 5H), 1.36-1.30 (m, 1H), 1.23-1.14 (m, 1H), 1.03 (s, 3H), 0.90 (s, 3H); $^{13}$C NMR (100 MHz, CDCl$_3$) δ 144.8 (C), 129.2 (q, J=32.6 Hz, C), 128.2 (CH), 125.2 (q, J=3.7 Hz, CH), 124.1 (q, J=270.5 Hz, C), 72.8 (CH), 68.4 (C), 47.8 (CH$_2$), 46.6 (C), 43.1 (CH), 39.5 (CH$_2$), 29.3 (CH$_2$), 26.9 (CH$_2$), 20.3 (CH$_3$), 19.8 (CH$_3$); IR (neat) 3392, 2955, 2879, 1324, 1124, 1066, 823 cm$^{-1}$; HRMS (EI) Calculated for C$_{17}$H$_{22}$F$_3$NO: 313.1653. Found: 313.1654.

PREPARATION EXAMPLE 2-10

Synthesis of (1S,2R,4R)-N-isopropyl-1-amino-2-exo-hydroxy-7,7-dimethyl-bicyclo[2.2.1]heptane (Compound 3j)

According to the synthesis method of preparation example 2, the procedure was followed by using compound 2 (0.3 g, 1.9 mmol), acetone (5.7 mmol), anhydrous dichloromethane (0.26 M, 7.4 ml), sodium triacetoxyborohydride (9.6 mmol), acetic acid (1.9 mmol). The reaction was worked up after 22 hr and purified by column chromatography on silica gel (EtOAc:hexanes=1:5 as eluant) to afford compound 3j (0.14 g) in 36% yield.

PREPARATION EXAMPLE 2-11

Synthesis of (1S,2R,4R)-N-isobutyl-1-amino-2-exo-hydroxy-7,7-dimethyl-bicyclo[2.2.1]heptane (Compound 3k)

According to the synthesis method of preparation example 2, the procedure was followed by using compound 2(0.3 g, 1.9 mmol), isobutyraldehyde (1.9 mmol), anhydrous dichloromethane (0.26 M, 7.4 ml), sodium triacetoxyborohydride (2.7 mmol), acetic acid (1.9 mmol). The reaction was worked up after 22 hr and purified by column chromatography on silica gel (EtOAc:hexanes=1:5 as eluant) to afford compound 3k (0.2 g) in 50% yield.

Synthesis of N-mono-substituted β-amino Alcohols (3l)

Reaction scheme 2:

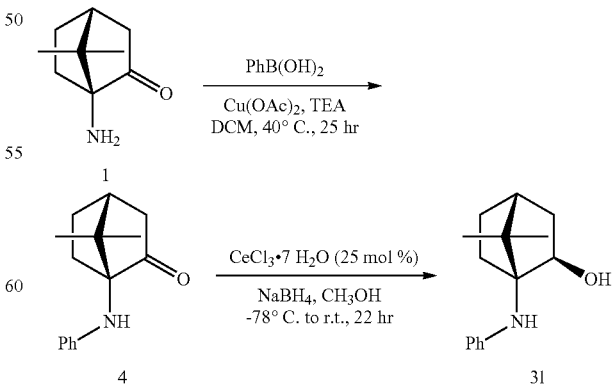

According to the reaction scheme 2, the starting material of the preparation reaction is (1S,4R)-1-amino-7,7-Dimethylbicyclo[2.2.1]heptan-2-one (compound 1), and the N-monosubstituted β-amino alcohol 3l were synthesized in two steps (Scheme 2).

PREPARATION EXAMPLE 3

Synthesis of (1S,4R)-N-phenyl-1-amino-7,7-dimethyl-bicyclo[2.2.1]heptane-2-one (Compound 4)

To a solution of (1S,4R)-1-amino-7,7-Dimethyl-bicyclo[2.2.1]heptan-2-one (compound 1) (1.0 g, 6.5 mmol) and phenyl boronic acid (2.0 equivant) in methylene chloride (43 mL, 0.15 M) was added copper acetate Cu(OAc)$_2$ (1.0 equivant) and triethylamine (2.0 equivant). The reaction mixture was stirred for 25 h at 40° C., then filtered with Celite and washed with ethyl acetate. The combined organic extracts were purified by column chromatography with EA/hexane (1/8) as eluent to give white solid (0.23 g, 16%). $^1$H NMR (400 MHz, CDCl$_3$) δ7.15-7.08 (m, 2H), 6.81-6.73 (m, 3H), 4.13 (br, 1H), 2.49-2.35 (m, 2H), 2.16-2.01 (m, 3H), 1.52-1.40 (m, 2H), 1.21 (s, 3H), 0.90 (s, 3H).

PREPARATION EXAMPLE 4

Synthesis of (1S,2R,4R)-N-phenyl-1-amino-2-exo-hydroxy-7,7-dimethyl-bicyclo[2.2.1]heptane (Compound 3l)

A solution of (1S,4R)-N-phenyl-1-amino-7,7-dimethyl-bicyclo[2.2.1]heptane-2-one (compound 4)(0.2 g, 0.87 mmol) and CeCl$_3$.7H$_2$O (81.2 mg, 0.21 mmol) in methanol (0.12 M, 7.0 mL) at −78° C. was added NaBH$_4$ (154.7 mg, 4.08 mmol). The temperature was raised to room temperature (25-28° C.). The reaction mixture was stirred for 22 h and then removed the methanol. Water (10 mL) was added and the aqueous phase was extracted with dichloromethane (10 mL×3). The combined organic extracts were washed with brine and dried over anhydrous sodium sulfate. Filtration and evaporated afforded a residue that was purified by column chromatography with EA/hexane (1/15) as eluent to give viscous liquid (0.2 g, 99%). $^1$H NMR (400 MHz, CDCl$_3$) δ7.16-7.12 (m, 2H), 6.77-6.73 (m, 3H), 4.13 (dd, J=8.0, 3.6 Hz, 1H), 3.50 (br, 1H), 2.55 (br, 1H), 1.98-1.93 (m, 1H), 1.89-1.73 (m, 4H), 1.62-1.55 (m, 1H), 1.27-1.21 (m, 1H), 1.13 (s, 3H), 0.96 (s, 3H).

REACTION EXAMPLE 1-1~1-11

The reaction scheme of enantioselective addition of organozinc to imines using the β-amino alcohol compounds 3a~3l of the following reaction examples 1-1~1-11 is as follows:

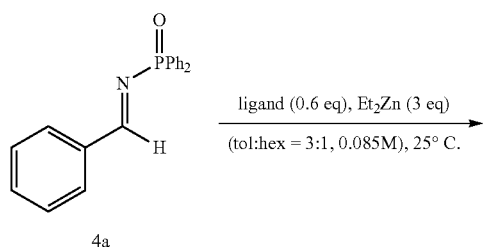

4a

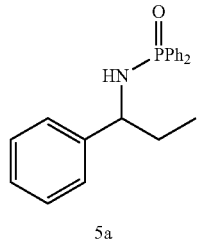

5a

REACTION EXAMPLE 1-1

The imine 4a (0.34 mmol) and 3a (50.1 mg, 0.2 mmol) were dissolved in toluene (3 mL), the mixture was cooled to 0° C., and Et$_2$Zn in hexanes (1.0 M, 1.02 mmol) was added. The temperature was raised to room temperature (25-28° C.) and stirred for 24 h and the reaction was quenched with aqueous ammonium chloride (4.0 mL), and added hydrochloric acid (1.0 N) to acidify the solution (pH=2). The aqueous layer was extracted with CH$_2$Cl$_2$ (10 mL×3) and the combined organic layers were dried over anhydrous Na$_2$SO$_4$. Concentration and purification by column chromatography (EA/Hex=1:5-1:0) gave the corresponding addition product 5a (N-[1-(phenyl)propyl]-P,P-diphenylphosphionylamide) with 91% yield and 93% enantiomeric excess (e.e.).

REACTION EXAMPLE 1-2

The experimental procedure of this reaction example was the same as that illustrated in reaction example 1-1, except that the compounds used for the enantioselective addition of organozinc to imines was compound 3a (56.2 mg, 0.2 mmol), and the reaction time is 48 h. The reaction gave the corresponding addition product 5a with 94% yield and 91% enantiomeric excess (e.e.).

REACTION EXAMPLE 1-3

The experimental procedure of this reaction example was the same as that illustrated in reaction example 1-1, except that the compounds used for the enantioselective addition of organozinc to imines was compound 3c (56.2 mg, 0.2 mmol), and the reaction time is 48 h. The reaction gave the corresponding addition product 5a with 99% yield and 94% enantiomeric excess (e.e.).

REACTION EXAMPLE 1-4

The experimental procedure of this reaction example was the same as that illustrated in reaction example 1-1, except that the compounds used for the enantioselective addition of organozinc to imines was compound 3d (56.2 mg, 0.2 mmol), and the reaction time is 48 h. The reaction gave the corresponding addition product 5a with 87% yield and 95% enantiomeric excess (e.e.).

REACTION EXAMPLE 1-5

The experimental procedure of this reaction example was the same as that illustrated in reaction example 1-1, except that the compounds used for the enantioselective addition of organozinc to imines was compound 3e (60.3 mg, 0.2 mmol), and the reaction time is 48 h. The reaction gave the corresponding addition product 5a with 91% yield and 95% enantiomeric excess (e.e.).

REACTION EXAMPLE 1-6

The experimental procedure of this reaction example was the same as that illustrated in reaction example 1-1, except that the compounds used for the enantioselective addition of organozinc to imines was compound 3f (60.3 mg, 0.2 mmol), and the reaction time is 48 h. The reaction gave the corresponding addition product 5a with 94% yield and 93% enantiomeric excess (e.e.).

REACTION EXAMPLE 1-7

The experimental procedure of this reaction example was the same as that illustrated in reaction example 1-1, except that the compounds used for the enantioselective addition of organozinc to imines was compound 3g (51.3 mg, 0.2 mmol), and the reaction time is 48 h. The reaction gave the corresponding addition product 5a with 93% yield and 92% enantiomeric excess (e.e.).

REACTION EXAMPLE 1-8

The experimental procedure of this reaction example was the same as that illustrated in reaction example 1-1, except that the compounds used for the enantioselective addition of organozinc to imines was compound 3h (53.8 mg, 0.2 mmol), and the reaction time is 45.5 h. The reaction gave the corresponding addition product 5a with 94% yield and 92% enantiomeric excess (e.e.).

REACTION EXAMPLE 1-9

The experimental procedure of this reaction example was the same as that illustrated in reaction example 1-1, except that the compounds used for the enantioselective addition of organozinc to imines was compound 3i (60.0 mg, 0.2 mmol), and the reaction time is 45.5 h. The reaction gave the corresponding addition product 5a with 92% yield and 91% enantiomeric excess (e.e.).

REACTION EXAMPLE 1-10

The experimental procedure of this reaction example was the same as that illustrated in reaction example 1-1, except that the compounds used for the enantioselective addition of organozinc to imines was compound 3j (40.3 mg, 0.2 mmol), and the reaction time is 48 h. The reaction gave the corresponding addition product 5a with 80% yield and 84% enantiomeric excess (e.e.).

REACTION EXAMPLE 1-11

The experimental procedure of this reaction example was the same as that illustrated in reaction example 1-1, except that the compounds used for the enantioselective addition of organozinc to imines was compound 3k (43.1 mg, 0.2 mmol), and the reaction time is 48 h. The reaction gave the corresponding addition product 5a with 82% yield and 90% enantiomeric excess (e.e.).

REACTION EXAMPLE 1-12

The experimental procedure of this reaction example was the same as that illustrated in reaction example 1-1, except that the compounds used for the enantioselective addition of organozinc to imines was compound 3l (47.2 mg, 0.2 mmol), and the reaction time is 48 h. The reaction gave the corresponding addition product 5a with 78% yield and 68% enantiomeric excess (e.e.), and the byproduct 6a (6% yield).

TABLE 1

| Reaction example | Amino alcohol compound | Reaction time (h) | Yield (%) | e.e (%) |
|---|---|---|---|---|
| 1-1 | 3a | 24 | 91 | 93 |
| 1-2 | 3b | 48 | 94 | 91 |
| 1-3 | 3c | 48 | 99 | 94 |
| 1-4 | 3d | 24 | 87 | 95 |
| 1-5 | 3e | 48 | 91 | 95 |
| 1-6 | 3f | 48 | 94 | 93 |
| 1-7 | 3g | 48 | 93 | 92 |
| 1-8 | 3h | 45.5 | 94 | 92 |
| 1-9 | 3i | 45.5 | 92 | 91 |
| 1-10 | 3j | 48 | 80 | 84 |
| 1-11 | 3k | 48 | 82 | 90 |
| 1-12 | 3l | 48 | 78 | 68 |

REACTION EXAMPLE 2-1~2-8

The reaction scheme of enantioselective addition of organozinc to imines using the β-amino alcohol compounds 3a of the following reaction examples 2-1~2-8 are as follows:

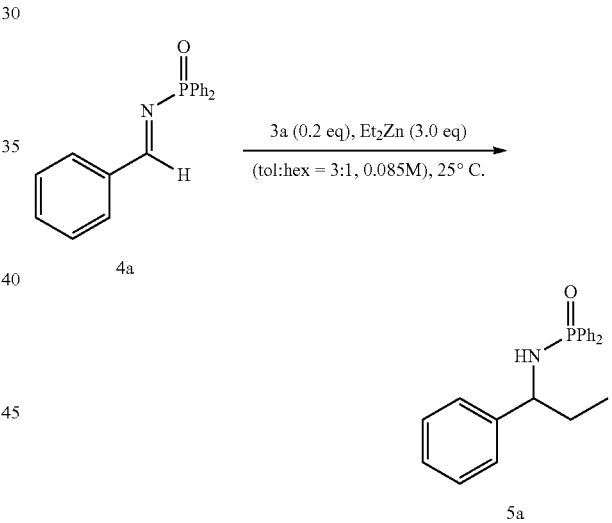

REACTION EXAMPLE 2-1

The imine 4a (0.34 mmol) and 3a (0.2 equivent) were dissolved in toluene (3.0 mL), and Et$_2$Zn in hexanes (1.0 M, 1.02 mmol) was added to the mixture under ice-bath condition. The temperature was raised to room temperature (25-28° C.) and stirred for 68.5 h and the reaction was quenched with aqueous ammonium chloride (4.0 mL), and added hydrochloric acid (1.0 N) to acidify the solution (pH=2). The aqueous layer was extracted with CH$_2$Cl$_2$ (10 mL×3) and the organic layers were dried over anhydrous Na$_2$SO$_4$. Concentration and purification by column chromatography (EA/Hex=1:5-1:0) gave the corresponding addition product 5a (N-[1-(phenyl)propyl]-P,P-diphenylphosphinyl amide) with 86% yield and 71% enantiomeric excess (e.e.).

REACTION EXAMPLE 2-2

The imine 4a (0.34 mmol) and 3a (0.2 equivent) were dissolved in toluene (3.0 mL), methanol (0.36 equivent, 5 μL) was added to the mixture as an additive, and then $Et_2Zn$ in hexanes (1.0 M, 1.02 mmol) was added to the mixture under ice-bath condition. The temperature was raised to room temperature (25-28° C.) and stirred for 24 h and the reaction was quenched with aqueous ammonium chloride (4.0 mL), and added hydrochloric acid (1.0 N) to acidify the solution (pH=2). The aqueous layer was extracted with $CH_2Cl_2$ (10 mL×3) and the organic layers were dried over anhydrous $Na_2SO_4$. Concentration and purification by column chromatography (EA/Hex=1:5-1:0) gave the corresponding addition product 5a with 87% yield and 77% enantiomeric excess (e.e.).

REACTION EXAMPLE 2-3

The experimental procedure of this reaction example was the same as that illustrated in reaction example 2-1, except that the additive added for the enantioselective addition of organozinc to imines was triisopropylsilyl chloride (TIPSCI, 0.96 equivent, 70 μL), and the reaction time was 43 h The reaction gave the corresponding addition product 5a with 76% yield and 70% enantiomeric excess (e.e.).

REACTION EXAMPLE 2-4

The experimental procedure of this reaction example was the same as that illustrated in reaction example 2-1, except that the additive added for the enantioselective addition of organozinc to imines was triisopropylsilyl chloride (TIPSCI, 0.96 equivent, 70 μL), the reaction time was 43 h, and the temperature was −20° C. The reaction gave the corresponding addition product 5a with 29% yield and 85% enantiomeric excess (e.e.).

REACTION EXAMPLE 2-5

The experimental procedure of this reaction example was the same as that illustrated in reaction example 2-1, except that the additive added for the enantioselective addition of organozinc to imines was trimethyl borate ($B(OMe)_3$, 0.26 equivent, 10 μL), and the reaction time was 43 h. The reaction gave the corresponding addition product 5a with 97% yield and 70% enantiomeric excess (e.e.).

REACTION EXAMPLE 2-6

The experimental procedure of this reaction example was the same as that illustrated in reaction example 2-1, except that the additive added for the enantioselective addition of organozinc to imines was trimethyl borate (0.92 equivent, 35 μL), and the reaction time was 48 h. The reaction gave the corresponding addition product 5a with 86% yield and 73% enantiomeric excess (e.e.).

REACTION EXAMPLE 2-7

The experimental procedure of this reaction example was the same as that illustrated in reaction example 2-1, except that the additive added for the enantioselective addition of organozinc to imines was Triphenylphosphine oxide ($Ph_3PO$, 0.4 equivent), and the reaction time was 24 h. The reaction gave the corresponding addition product 5a with 99% yield and 53% enantiomeric excess (e.e.).

REACTION EXAMPLE 2-8

The experimental procedure of this reaction example was the same as that illustrated in reaction example 2-1, except that the additive added for the enantioselective addition of organozinc to imines was Triphenylphosphine oxide (1.0 equivent), and the reaction time was 24 h. The reaction gave the corresponding addition product 5a with 99% yield and 44% enantiomeric excess (e.e.).

TABLE 2

| Reaction example | Additive (equivent) | Reaction time (h) | yield (%) | e.e (%) |
|---|---|---|---|---|
| 2-1 | — | 68.5 | 86 | 71 |
| 2-2 | MeOH (0.36) | 24 | 87 | 77 |
| 2-3 | TIPSCI (0.96) | 43 | 76 | 70 |
| 2-4[a] | TIPSCI (0.96) | 43 | 29 | 85 |
| 2-5 | $B(OMe)_3$ (0.26) | 48 | 97 | 70 |
| 2-6 | $B(OMe)_3$ (0.92) | 48 | 86 | 73 |
| 2-7 | $Ph_3PO$ (0.4) | 24 | 99[b] | 53 |
| 2-8 | $Ph_3PO$ (1.0) | 24 | 99[b] | 44 |

[a]Reaction temperature was −20° C.
[b]Evaluated by Proton Nuclear Magnetic Resonance ($H^1$-NMR).

As shown in Table 2, preferably, the additive used in the present invention is methanol, trimethyl borate, triisopropylsilyl chloride, and triphenylphosphine oxide; and most preferably, the additive used in the present invention is methanol.

REACTION EXAMPLES 3-1~3-19

The reaction scheme of enantioselective addition of organozinc to imines using the β-amino alcohol compound 3a and using alcohols as additive of the following reaction examples 3-1~3-19 are as follows:

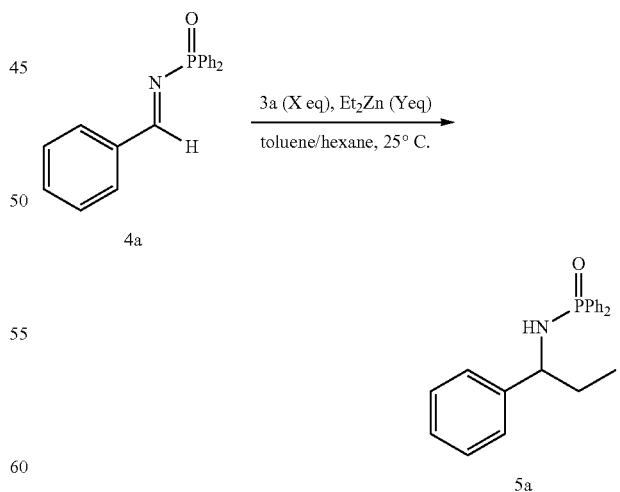

REACTION EXAMPLE 3-1

The imine 4a (0.34 mmol) and 3a (0.6 equivent) were dissolved in toluene (3.0 mL), and $Et_2Zn$ in hexanes (1.0 M, 3 equivent) was added to the mixture under ice-bath condition. The temperature was raised to room temperature (25-28° C.) and stirred for 24 h and the reaction was quenched with aqueous ammonium chloride (4.0 mL), and added hydrochloric acid (1.0 N) to acidify the solution (pH=2). The aqueous layer was extracted with $CH_2Cl_2$ (10 mL×3) and the organic layers were dried over anhydrous $Na_2SO_4$. Concentration and purification by column chromatography (EA/Hex=1:5-1:0) gave the corresponding addition product 5a with 91% yield and 93% enantiomeric excess (e.e.).

REACTION EXAMPLE 3-2

The imine 4a (0.34 mmol) and 3a (0.2 equivent) were dissolved in toluene (3.0 mL), and $Et_2Zn$ in hexanes (1.0 M, 3 equivent) was added to the mixture under ice-bath condition. The temperature was raised to room temperature (25-28° C.) and stirred for 68.5 h and the reaction was quenched with aqueous ammonium chloride (4.0 mL), and added hydrochloric acid (1.0 N) to acidify the solution (pH=2). The aqueous layer was extracted with $CH_2Cl_2$ (10 mL×3) and the organic layers were dried over anhydrous $Na_2SO_4$. Concentration and purification by column chromatography (EA/Hex=1:5-1:0) gave the corresponding addition product 5a with 86% yield and 71% enantiomeric excess (e.e.).

REACTION EXAMPLE 3-3

The imine 4a (0.34 mmol) and 3a (0.6 equivent) were dissolved in toluene (3.0 mL), methanol (0.72 equivent, 10 µL) was added as additive, and $Et_2Zn$ in hexanes (1.0 M, 3 equivent) was added to the mixture under ice-bath condition. The temperature was raised to room temperature (25-28° C.) and stirred for 24 h and the reaction was quenched with aqueous ammonium chloride (4.0 mL), and added hydrochloric acid (1.0 N) to acidify the solution (pH=2). The aqueous layer was extracted with $CH_2Cl_2$ (10 mL×3) and the organic layers were dried over anhydrous $Na_2SO_4$. Concentration and purification by column chromatography (EA/Hex=1:5-1:0) gave the corresponding addition product 5a with 96% yield and 95% enantiomeric excess (e.e.).

REACTION EXAMPLE 3-4

The imine 4a (0.34 mmol) and 3a (0.2 equivent) were dissolved in toluene (3.0 mL), methanol (0.36 equivent, 5 µL) was added as additive, and $Et_2Zn$ in hexanes (1.0 M, 3.0 equivent) was added to the mixture under ice-bath condition. The temperature was raised to room temperature (25-28° C.) and stirred for 24 h and the reaction was quenched with aqueous ammonium chloride (4.0 mL), and added hydrochloric acid (1.0 N) to acidify the solution (pH=2). The aqueous layer was extracted with $CH_2Cl_2$ (10 mL×3) and the organic layers were dried over anhydrous $Na_2SO_4$. Concentration and purification by column chromatography (EA/Hex=1:5-1:0) gave the corresponding addition product 5a with 87% yield and 77% enantiomeric excess (e.e.).

REACTION EXAMPLE 3-5

The experimental procedure of this reaction example was the same as that illustrated in reaction example 3-3, except that the equivent of the β-amino alcohol compound 3a was 0.2. The reaction gave the corresponding addition product 5a with 91% yield and 83% enantiomeric excess (e.e.).

REACTION EXAMPLE 3-6

The experimental procedure of this reaction example was the same as that illustrated in reaction example 3-4, except that the equivent of the additive methanol was 1.08 (15 µL). The reaction gave the corresponding addition product 5a with 81% yield and 88% enantiomeric excess (e.e.).

REACTION EXAMPLE 3-7

The experimental procedure of this reaction example was the same as that illustrated in reaction example 3-4, except that the equivent of the additive methanol was 2.17 (30 µL), and the reaction time was 45 h. The reaction gave the corresponding addition product 5a with 21% yield and 70% enantiomeric excess (e.e.).

REACTION EXAMPLE 3-8

The experimental procedure of this reaction example was the same as that illustrated in reaction example 3-4, except that the equivent of the additive methanol was 2.90 (40 µL), and the reaction time was 45 h. However, the reaction gave no yield of the addition product 5a.

REACTION EXAMPLE 3-9

The experimental procedure of this reaction example was the same as that illustrated in reaction example 3-4, except that the equivent of $Et_2Zn$ was 3.5, and the equivent of the additive methanol was 1.08 (15 µL). The reaction gave the corresponding addition product 5a with $90(4)^a$% yield and 88% enantiomeric excess (e.e.).

REACTION EXAMPLE 3-10

The experimental procedure of this reaction example was the same as that illustrated in reaction example 3-4, except that the equivent of $Et_2Zn$ was 4.0, and the equivent of the additive methanol was 1.08 (15 µL). The reaction gave the corresponding addition product 5a with $90(5)^a$% yield and 87% enantiomeric excess (e.e.).

REACTION EXAMPLE 3-11

The experimental procedure of this reaction example was the same as that illustrated in reaction example 3-4, except that the equivent of $Et_2Zn$ was 5.0, and the equivent of the additive methanol was 1.08 (15 µL). The reaction gave the corresponding addition product 5a with $89(6)^a$% yield and 88% enantiomeric excess (e.e.).

REACTION EXAMPLE 3-12

The experimental procedure of this reaction example was the same as that illustrated in reaction example 3-4, except that the equivent of $Et_2Zn$ was 5.0, and the additive methanol was 1.45 (20 µL). The reaction gave the corresponding addition product 5a with 90% yield and 92% enantiomeric excess (e.e.).

REACTION EXAMPLE 3-13

The experimental procedure of this reaction example was the same as that illustrated in reaction example 3-4, except that the equivent of $Et_2Zn$ was 5.0, and the equivent of the additive methanol was 1.81 (25 µL). The reaction gave the corresponding addition product 5a with 90% yield and 93% enantiomeric excess (e.e.).

REACTION EXAMPLE 3-14

The experimental procedure of this reaction example was the same as that illustrated in reaction example 3-4, except that the equivent of Et$_2$Zn was 8.1, and the equivent of the additive methanol was 2.53 (35 μL). The reaction gave the corresponding addition product 5a with 85% yield and 95% enantiomeric excess (e.e.).

REACTION EXAMPLE 3-15

The imine 4a (0.34 mmol) and 3a (0.2 equivent) were dissolved in toluene (3.0 mL), ethanol (1.75 equivent, 35 μL) was added as additive, and Et$_2$Zn in hexanes (1.0 M, 5.0 equivent) was added to the mixture under ice-bath condition. The temperature was raised to room temperature (25-28° C.) and stirred for 24 h and the reaction was quenched with aqueous ammonium chloride (4.0 mL), and added hydrochloric acid (1.0 N) to acidify the solution (pH=2). The aqueous layer was extracted with CH$_2$Cl$_2$ (10 mL×3) and the organic layers were dried over anhydrous Na$_2$SO$_4$. Concentration and purification by column chromatography (EA/Hex=1:5-1:0) gave the corresponding addition product 5a with 86% yield and 86% enantiomeric excess (e.e.).

REACTION EXAMPLE 3-16

The experimental procedure of this reaction example was the same as that illustrated in reaction example 3-15, except that the additive was isopropanol (1.72 equivent, 45 μL). The reaction gave the corresponding addition product 5a with 95% yield and 73% enantiomeric excess (e.e.).

REACTION EXAMPLE 3-17

The experimental procedure of this reaction example was the same as that illustrated in reaction example 3-15, except that the additive was water (0.81 equivent, 5 μL), and the reaction time was 48 h. The reaction gave the corresponding addition product 5a with 54% yield and 81% enantiomeric excess (e.e.).

REACTION EXAMPLE 3-18

The experimental procedure of this reaction example was the same as that illustrated in reaction example 3-13, except that the equivent of β-amino alcohol compound 3a was 0.1. The reaction gave the corresponding addition product 5a with 86% yield and 91% enantiomeric excess (e.e.).

REACTION EXAMPLE 3-19

The experimental procedure of this reaction example was the same as that illustrated in reaction example 3-13, except that the equivent of β-amino alcohol compound 3a was 0.05, and the reaction time was 48 h. The reaction gave the corresponding addition product 5a with 82% yield and 86% enantiomeric excess (e.e.).

TABLE 3

| Reaction example | β-amino alcohol compound 3a (equivent X) | Et$_2$Zn (equivent Y) | Additive (equivent) | Reaction time (h) | Yield (%) | e.e. (%) |
|---|---|---|---|---|---|---|
| 3-1 | 0.6 | 3 | — | 24 | 91 | 93 |
| 3-2 | 0.2 | 3 | — | 68.5 | 86 | 71 |
| 3-3 | 0.6 | 3 | methanol (0.72) | 24 | 96 | 95 |
| 3-4 | 0.2 | 3 | methanol (0.36) | 24 | 87 | 77 |
| 3-5 | 0.2 | 3 | methanol (0.72) | 24 | 91 | 83 |
| 3-6 | 0.2 | 3 | methanol (1.08) | 24 | 81 | 88 |
| 3-7 | 0.2 | 3 | methanol (2.17) | 45 | 21 | 70 |
| 3-8 | 0.2 | 3 | methanol (2.90) | 45 | — | — |
| 3-9 | 0.2 | 3.5 | methanol (1.08) | 24 | 90(4)$^a$ | 88 |
| 3-10 | 0.2 | 4 | methanol (1.08) | 24 | 90(5)$^a$ | 87 |
| 3-11 | 0.2 | 5 | methanol (1.08) | 24 | 89(6)$^a$ | 88 |
| 3-12 | 0.2 | 5 | methanol (1.45) | 24 | 90 | 92 |
| 3-13 | 0.2 | 5 | methanol (1.81) | 24 | 90 | 93 |
| 3-14 | 0.2 | 8.1 | methanol (2.53) | 24 | 85 | 95 |
| 3-15 | 0.2 | 5 | ethanol (1.75) | 24 | 86 | 86 |
| 3-16 | 0.2 | 5 | isopropanol (1.72) | 24 | 95 | 73 |
| 3-17 | 0.2 | 5 | Water (H$_2$O) (0.81) | 48 | 54 | 81 |
| 3-18 | 0.1 | 5 | methanol (1.81) | 24 | 86 | 91 |
| 3-19 | 0.05 | 5 | methanol (1.81) | 48 | 82 | 86 |

$^a$Yield of the reduction product.

According the Table 3, preferably, when methanol was used as an additive, the additive was used in an amount of 0.1 to 3 equivent based on R$_2$CH=NY; and more preferably, the additive was used in an amount of 0.1 to 3 equivent.

REACTION EXAMPLES 4-1~4-14

The reaction scheme of enantioselective addition of organozinc to imines using the β-amino alcohol compound 3a and using alcohols as additive of the following reaction examples 4-1~4-14 are as follows:

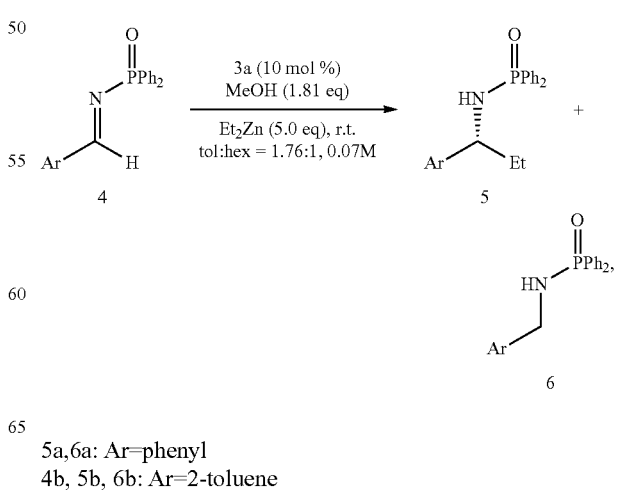

5a,6a: Ar=phenyl
4b, 5b, 6b: Ar=2-toluene 4c, 5c, 6c: Ar=3-toluene
4d, 5d, 6d: Ar=4-toluene
4e, 5e, 6e: Ar=2-methoxyl-phenyl
4f, 5f, 6f: Ar=3-methoxyl-phenyl
4g, 5g, 6g: Ar=4-methoxyl-phenyl
4h, 5h, 6h: Ar=2-chlorophenyl
4i, 5i, 6i: Ar=3-chlorophenyl
4j, 5j, 6j: Ar=4-chlorophenyl
4k, 5k, 6k: Ar=4-methylcarbonyl-phenyl

REACTION EXAMPLE 4-1

The imine 4a (0.34 mmol) and 3a (0.034 equivent) were dissolved in toluene (3.0 mL) under argon atmospheous, and methanol (25 µL, 0.61 mmol) was added, and then the mixture was stirred for 10 min at room temperature (25-28° C.). The solution was cooled to 0° C., and $Et_2Zn$ in hexanes (1.0 M, 1.7 mL, 1.7 mmol) was added dropwise to the mixture under ice-bath condition. The temperature was raised to room temperature (25-28° C.) and stirred for 24-44 h and the reaction was quenched with aqueous ammonium chloride (4.0 mL), and added hydrochloric acid (1.0 N) to acidify the solution (pH=2). The aqueous layer was extracted with $CH_2Cl_2$ (10 mL×3) and the organic layers were dried over anhydrous $Na_2SO_4$. Concentration and purification by column chromatography (EA/Hex=1:5-1:0) gave the corresponding addition product 5a (white solid) with 86% yield and 91% enantiomeric excess (e.e.), and gave the byproduct 6a with 1% yield. $^1$H NMR (400 MHz, $CDCl_3$): δ 7.86-7.81 (m, 2H), 7.74-7.69 (m, 2H), 7.46-7.36 (m, 4H), 7.31-7.18 (m, 5H), 7.12 (d, J=7.2 Hz, 2H), 4.10-4.02 (m, 1H), 3.28-3.24 (m, 1H), 2.01-1.92 (m, 1H), 1.85-1.75 (m, 1H), 0.76 (t, J=7.2 Hz, 3H); $^{13}$C NMR (100 MHz, $CDCl_3$): δ 143.45 (d, J=5.1 Hz, C), 132.55, 132.45, 131.78, 131.69, 131.59, 128.42, 128.37, 128.29, 128.24, 128.12, 126.97, 126.44, 57.05 (CH), 32.44 (d, J=3.7 Hz, $CH_2$), 10.5 ($CH_3$); IR (neat): 3172, 1187 $cm^{-1}$; HRMS (FAB) Calculated for $C_{21}H_{23}NOP$ ([M+H]$^+$) 336.1517, found: 336.1522. The enantiomeric excess of 91% with R-isomer major was determined by HPLC (Chiralcel® OD-H column, Hexane/2-propanol=95:5; flow rate 1.0 mL/min; R-isomer, $t_R$ 9.66 min and S-isomer, $t_R$ 13.68 min).

REACTION EXAMPLE 4-2

The experimental procedure of this reaction example was the same as that illustrated in reaction example 4-1, except that the β-amino alcohol compound 3a was replaced by (1S, 2R)-7,7-dimethyl-1-morpholin-4-yl-bicyclo[2.2.1]heptan-2-ol ((+)-MINBOL). The reaction gave the corresponding addition product 5a with 76% yield and 86% enantiomeric excess (e.e.).

REACTION EXAMPLE 4-3

The experimental procedure of this reaction example was the same as that illustrated in reaction example 4-1, except that the β-amino alcohol compound 3a was replaced by (+)-MINBOL (5 mol %) and β-amino alcohol compound 3a (5 mol %), and the reaction time was 24 h. The reaction gave the corresponding addition product 5a with 80% yield and 89% enantiomeric excess (e.e.).

REACTION EXAMPLE 4-4

The experimental procedure of this reaction example was the same as that illustrated in reaction example 4-1, except that the imime 4a was replaced by imine 4b, and the reaction time was 41 h. The reaction gave the corresponding addition product 5b (N-[1-(2-Methylphenyl)propyl]-P,P-diphenylphosphinoylamide, white solid) with 60% yield and 89% enantiomeric excess (e.e.). $^1$H NMR (400 MHz, $CDCl_3$) δ 7.86-7.81 (m, 2H), 7.68-7.63 (m, 2H), 7.45-7.19 (m, 8H), 7.09 (t, J=7.2 Hz, 1H), 6.97-6.96 (m, 1H), 4.35-4.26 (m, 1H), 3.37-3.32 (m, 1H), 1.93-1.88 (m, 1H), 1.85 (s, 3H), 1.8-1.69 (m, 1H), 0.81 (t, J=7.2 Hz, 3H); $^{13}$C NMR (100 MHz, $CDCl_3$) δ 142.36 (d, J=5.1 Hz, C), 134.72 (C), 132.55, 132.46, 131.75, 131.67, 131.52, 131.15, 130.07, 128.42, 128.30, 128.16, 128.03, 126.57, 126.28, 125.18, 52.29 (CH), 32.64 ($CH_2$), 18.9 ($CH_3$), 10.44 ($CH_3$); IR (neat) 3183, 1188 $cm^{-1}$; HRMS (FAB) Calculated for $C_{22}H_{25}NOP$ ([M+H]$^+$): 350.1674. Found: 350.1679. The enantiomeric excess of 89% with R-isomer major was determined by HPLC (Chiralcel® OD-H column, Hexane/2-propanol=95:5; flow rate 1.0 mL/min; R-isomer, $t_R$ 9.21 min and S-isomer, $t_R$ 15.04 min).

REACTION EXAMPLE 4-5

The experimental procedure of this reaction example was the same as that illustrated in reaction example 4-1, except that the imime 4a was replaced by imine 4c, and the reaction time was 44 h. The reaction gave the corresponding addition product 5c (N-[1-(3-Methylphenyl)propyl]-P,P-diphenylphosphinoylamide, white solid) with 76% yield and 89% enantiomeric excess (e.e.), and gave the byproduct 6c with 8% yield. $^1$H NMR (400 MHz, $CDCl_3$) δ 7.85-7.8 (m, 2H), 7.75-7.7 (m, 2H), 7.46-7.35 (m, 4H), 7.32-7.27 (m, 2H), 7.15 (t, J=7.6 Hz, 1H), 7.02-7.0 (m, 1H), 6.95-6.93 (m, 1H), 6.88 (s, 1H), 4.03-4.0 (m, 1H), 3.27-3.26 (m, 1H), 2.27 (s, 3H), 2.0-1.94 (m, 1H), 1.83-1.76 (m, 1H), 0.74 (t, J=7.6 Hz, 3H); $^{13}$C NMR (100 MHz, $CDCl_3$) δ 143.3 (d, J=5.8 Hz, C), 137.87 (C), 133.93, 132.58, 132.49, 131.76, 131.67, 131.54, 131.35, 128.39, 128.26, 128.19, 128.07, 127.75, 127.27, 123.42, 57.09 (CH), 32.34 (d, J=2.9 Hz, $CH_2$), 21.38 ($CH_3$), 10.56 ($CH_3$); IR (neat) 3183, 1188 $cm^{-1}$; HRMS (FAB) Calculated for $C_{22}H_{25}NOP$ ([M+H]$^+$): 350.1674. Found: 350.1680. The enantiomeric excess of 89% with R-isomer major was determined by HPLC (Chiralcel® AD-H column, Hexane/2-propanol=80:20; flow rate 0.8 mL/min; R-isomer, $t_R$ 7.85 min and S-isomer, $t_R$ 13.11 min).

REACTION EXAMPLE 4-6

The experimental procedure of this reaction example was the same as that illustrated in reaction example 4-1, except that the imime 4a was replaced by imine 4d, and the reaction time was 30 h. The reaction gave the corresponding addition product 5d (N-[1-(4-Methylphenyl)propyl]-P,P-diphenylphosphinoylamide, white solid) with 83% yield and 92% enantiomeric excess (e.e.), and gave the byproduct 6d with 4% yield. $^1$H NMR (400 MHz, $CDCl_3$) δ 7.85-7.8 (m, 2H), 7.75-7.70 (m, 2H), 7.42-7.32 (m, 4H), 7.30-7.25 (m, 2H), 7.07-7.01 (m, 4H), 4.05-3.97 (m, 1H), 3.31-3.29 (m, 1H), 2.28 (s, 3H), 2.02-1.92 (m, 1H), 1.84-1.73 (m, 1H), 0.74 (t, J=7.2 Hz, 3H); $^{13}$C NMR (100 MHz, $CDCl_3$) δ 140.39 (d, J=5.9 Hz, C), 136.40, 132.63, 132.46, 132.37, 131.72, 131.63, 131.54, 131.44, 128.95, 128.29, 128.16, 128.02, 126.27, 56.78 (CH), 32.31 (d, J=3 Hz, $CH_2$), 20.91 ($CH_3$), 10.48 ($CH_3$); IR (neat) 3183, 1187 $cm^{-1}$; HRMS (FAB) Calculated for $C_{22}H_{25}NOP$ ([M+H]$^+$): 350.1674. Found: 350.1672. The enantiomeric excess of 92% with R-isomer major was determined by HPLC (Chiralcel® OD-H column, Hexane/2-propanol=98:2; flow rate 0.8 mL/min; R-isomer, $t_R$ 11.84 min and S-isomer, $t_R$ 14.24 min).

REACTION EXAMPLE 4-7

The experimental procedure of this reaction example was the same as that illustrated in reaction example 4-1, except that the imime 4a was replaced by imine 4e, and the reaction time was 44 h. The reaction gave the corresponding addition product 5e (N-[1-(2-Methoxyphenyl)propyl]-P,P-diphenylphosphinoylamide, white solid) with 71% yield and 87% enantiomeric excess (e.e.), and gave the byproduct 6e with 28% yield. $^1$H NMR (400 MHz, CDCl$_3$) δ 7.84-7.79 (m, 2H), 7.74-7.68 (m, 2H), 7.43-7.34 (m, 4H), 7.13-7.26 (m, 2H), 7.21-7.17 (m, 1H), 6.93-6.91 (m, 1H), 6.86-6.81 (m, 2H), 4.16-4.07 (m, 1H), 4.0-3.95 (m, 1H), 3.7 (s, 3H), 2.01-1.93 (m, 1H), 1.92-1.83 (m, 1H), 0.74(t, J=7.2 Hz, 3H); $^{13}$C NMR (100 MHz, CDCl$_3$) δ 156.92, 132.93, 132.64, 132.55, 131.78, 131.68, 131.56, 131.43, 128.51, 128.38, 128.26, 128.15, 128.03, 120.50, 110.93, 55.4 (CH$_3$), 55.13 (CH), 30.94 (d, J=3.7 Hz, CH$_2$), 11.13 (CH$_3$); IR (neat) 3202, 1191 cm$^{-1}$; HRMS (EI) Calculated for C$_{20}$H$_{19}$NO$_2$P ([M-CH$_2$CH$_3$]$^+$): 366.1148. Found: 366.1153. The enantiomeric excess of 87% with R-isomer major was determined by HPLC (Chiralcel® AD-H column, Hexane/2-propanol=80:20; flow rate 0.8 mL/min; R-isomer, t$_R$ 12.00 min and S-isomer, t$_R$ 14.35 min).

REACTION EXAMPLE 4-8

The experimental procedure of this reaction example was the same as that illustrated in reaction example 4-1, except that the imime 4a was replaced by imine 4e, and without the presence of methanol. The reaction gave the corresponding addition product 5e with 52% yield and 79% enantiomeric excess (e.e.), and gave the byproduct 6e with 47% yield.

REACTION EXAMPLE 4-9

The experimental procedure of this reaction example was the same as that illustrated in reaction example 4-1, except that the imime 4a was replaced by imine 4f, and the reaction time was 30 h. The reaction gave the corresponding addition product 5f (N-[1-(3-Methoxyphenyl)propyl]-P,P-diphenylphosphinoylamide, white solid) with 87% yield and 88% enantiomeric excess (e.e.), and gave the byproduct 6f with 6% yield. $^1$H NMR (400 MHz, CDCl$_3$) δ 7.84-7.79 (m, 2H), 7.74-7.69 (m, 2H), 7.44-7.34 (m, 4H), 7.30-7.26 (m, 2H), 7.17 (t, J=8 Hz, 1H), 6.74-6.71 (m, 2H), 6.65 (t, J=2 Hz, 1H), 4.06-3.98 (m, 1H), 3.71 (s, 3H), 3.34-3.3 (m, 1H), 1.99-1.9 (m, 1H), 1.84-1.73 (m, 1H), 0.75 (t, J=7.2 Hz, 3H); $^{13}$C NMR (100 MHz, CDCl$_3$) δ 159.51 (C), 145.12 (d, J=5.1 Hz, C), 133.83, 132.54, 132.44, 131.74, 131.64, 131.56, 131.29, 129.38, 128.39, 128.26, 128.20, 128.07, 118.73, 112.39, 112.09, 57.02 (CH), 55.05 (CH$_3$), 32.29 (d, J=3 Hz, CH$_2$), 10.49 (CH$_3$); IR (neat) 3180, 1187 cm$^{-1}$; HRMS (FAB) Calculated for C$_{22}$H$_{25}$NO$_2$P ([M+H]$^+$): 366.1623. Found: 366.1624. The enantiomeric excess of 88% with R-isomer major was determined by HPLC (Chiralcel® AD-H column, Hexane/2-propanol=80:20; flow rate 1.0 mL/min; R-isomer, t$_R$ 8.11 min and S-isomer, t$_R$ 15.32 min).

REACTION EXAMPLE 4-10

The experimental procedure of this reaction example was the same as that illustrated in reaction example 4-1, except that the imime 4a was replaced by imine 4g, and the reaction time was 30 h. The reaction gave the corresponding addition product 5g (N-[1-(4-Methoxyphenyl)propyl]-P,P-diphenylphosphinoylamide, white solid) with 86% yield and 91% enantiomeric excess (e.e.). $^1$H NMR (400 MHz, CDCl$_3$) δ 7.85-7.8 (m, 2H), 7.75-7.7 (m, 2H), 7.45-7.36 (m, 4H), 7.32-7.27 (m, 2H), 7.04 (d, J=8.8 Hz, 2H), 6.79 (d, J=8.4 Hz, 2H), 4.05-3.95 (m, 1H), 3.75 (s, 3H), 3.25-3.21 (m, 1H), 1.99-1.91 (m, 1H), 1.8-1.73 (m, 1H), 0.73 (t, J=7.2 Hz, 3H); $^{13}$C NMR (100 MHz, CDCl$_3$) δ 158.46 (C), 135.59 (d, J=5.9 Hz, C), 132.52, 132.43, 131.78, 131.69, 131.54, 128.4, 128.28, 128.12, 127.55, 113.7, 56.54 (CH), 55.15 (CH$_3$), 32.38 (CH$_2$), 10.57 (CH$_3$); IR (neat) 3190, 1180 cm$^{-1}$; HRMS (FAB) Calculated for C$_{22}$H$_{25}$NO$_2$P ([M+H]$^+$): 366.1623. Found: 366.1620.The enantiomeric excess of 91% with R-isomer major was determined by HPLC (Chiralcel® AD-H column, Hexane/2-propanol=80:20; flow rate 1.0 mL/min; R-isomer, t$_R$ 11.95 min and S-isomer, t$_R$ 15.07 min).

REACTION EXAMPLE 4-11

The experimental procedure of this reaction example was the same as that illustrated in reaction example 4-1, except that the imime 4a was replaced by imine 4h, and the reaction time was 41 h. The reaction gave the corresponding addition product 5h (N-[1-(2-Chlorophenyl)propyl]-P,P-diphenylphosphinoylamide, white solid) with 68% yield and 84% enantiomeric excess (e.e.), and gave the byproduct 6h with 24% yield. $^1$H NMR (400 MHz, CDCl$_3$) δ 7.83-7.78 (m, 2H), 7.69-7.63 (m, 2H), 7.43-7.32 (m, 4H), 7.27-7.16 (m, 5H), 7.12-7.07 (m, 1H), 4.49-4.41 (m, 1H), 3.74-3.70 (m, 1H), 1.94-1.80 (m, 2H), 0.82(t, J=7.2 Hz, 3H); $^{13}$C NMR (100 MHz, CDCl$_3$) δ 140.96 (d, J=4.4 Hz, C), 133.43, 132.38, 132.28, 132.15, 131.74, 131.64, 131.51, 130.99, 129.51, 128.37, 128.24, 128.13, 128.01, 127.93, 126.81, 54.36(CH), 31.38 (d, J=3.7 Hz, CH$_2$), 10.49 (CH$_3$); IR (neat) 3172, 1186 cm$^{-1}$; HRMS (FAB) Calculated for C$_{21}$H$_{22}$ClNOP ([M+H]$^+$): 370.1128. Found: 370.1139. The enantiomeric excess of 84% with R-isomer major was determined by HPLC (Chiralcel® AS-H column, Hexane/2-propanol=85:15; flow rate 1.0 mL/min; R-isomer, t$_R$ 13.94 min and S-isomer, t$_R$ 26.73 min).

REACTION EXAMPLE 4-12

The experimental procedure of this reaction example was the same as that illustrated in reaction example 4-1, except that the imime 4a was replaced by imine 4i, and the reaction time was 43 h. The reaction gave the corresponding addition product 5i (N-[1-(3-Chlorophenyl)propyl]-P,P-diphenylphosphinoylamide, white solid) with 84% yield and 85% enantiomeric excess (e.e.), and gave the byproduct 6i with 6% yield. $^1$H NMR (400 MHz, CDCl$_3$) δ 7.84-7.79 (m, 2H), 7.71-7.66 (m, 2H), 7.46-7.35 (m, 4H), 7.30-7.26 (m, 2H), 7.15-7.12 (m, 2H), 7.09 (s, 1H), 7.01-6.97 (m, 1H), 4.07-3.98 (m, 1H), 3.42-3.38 (m, 1H), 1.97-1.88 (m, 1H), 1.82-1.71 (m, 1H), 0.76 (t, J=7.2 Hz, 3H); $^{13}$C NMR (100 MHz, CDCl$_3$) δ 145.65 (d, J=5.1 Hz, C), 134.13, 133.48, 132.44, 132.35, 132.21, 131.78, 131.68, 129.62, 128.48, 128.35, 128.25, 128.12, 127.11, 126.63, 124.83, 56.56 (CH), 32.25 (d, J=3.6 Hz, CH$_2$), 10.46 (CH$_3$); IR (neat) 3170, 1186 cm$^{-1}$; HRMS (FAB) Calculated for C$_{21}$H$_{22}$ClNOP ([M+H]$^+$): 370.1128. Found: 370.1120. The enantiomeric excess of 85% with R-isomer major was determined by HPLC (Chiralcel® OD-H column, Hexane/2-propanol=95:5; flow rate 1.0 mL/min; R-isomer, t$_R$ 10.05 min and S-isomer, t$_R$ 13.83 min).

REACTION EXAMPLE 4-13

The experimental procedure of this reaction example was the same as that illustrated in reaction example 4-1, except that the imime 4a was replaced by imine 4j, and the reaction time was 30 h. The reaction gave the corresponding addition product 5j (N-[1-(4-Chlorophenyl)propyl]-P,P-diphenylphosphinoylamide, white solid) with 86% yield and 89% enantiomeric excess (e.e.), and gave the byproduct 6j with 3% yield. $^1$H NMR (400 MHz, CDCl$_3$) δ 7.84-7.79 (m, 2H), 7.72-7.66 (m, 2H), 7.48-7.36 (m, 4H), 7.32-7.27 (m, 2H), 7.24-7.19 (m, 2H), 7.06-7.04 (m, 2H), 4.08-4.0 (m, 1H), 3.29-3.25 (m, 1H), 2.0-1.88 (m, 1H), 1.81-1.70 (m, 1H), 0.76 (t, J=7.2 Hz, 3H); $^{13}$C NMR (100 MHz, CDCl$_3$) δ 142.06 (d, J=5.1 Hz, C), 133.53, 132.66, 132.45, 132.36, 132.27, 131.82, 131.73, 131.24, 128.50, 128.40, 128.33, 128.20, 127.92, 56.43 (CH), 32.33 (d, J=4.4 Hz, CH$_2$), 10.46 (CH$_3$); IR (neat) 3171, 1185 cm$^{-1}$; HRMS (FAB) Calculated for C$_{21}$H$_{22}$ClNOP ([M+H]$^+$): 370.1128. Found: 370.1117. The enantiomeric excess of 89% with R-isomer major was determined by HPLC (Chiralcel® OD-H column, Hexane/2-propanol=95:5; flow rate 0.8 mL/min; R-isomer, $t_R$ 13.37 min and S-isomer, $t_R$ 16.23 min).

REACTION EXAMPLE 4-14

The experimental procedure of this reaction example was the same as that illustrated in reaction example 4-1, except that the imime 4a was replaced by imine 4k, and the reaction time was 40 h. The reaction gave the corresponding addition product 5k (Methyl 4-[P,P-1-(diphenylphosphinylamido)propyl]benzoate, white solid) with 92% yield and 84% enantiomeric excess (e.e.). $^1$H NMR (400 MHz, CDCl$_3$) δ 7.92-7.90 (m, 2H), 7.84-7.79 (m, 2H), 7.70-7.65 (m,2H), 7.47-7.43 (m, 1H), 7.41-7.36 (m, 3H), 7.28-7.24 (m, 2H), 7.20-7.17 (m, 2H), 4.17-4.05 (m, 1H), 3.87 (s, 3H), 3.39-3.35 (m, 1H), 2.01-1.90 (m, 1H), 1.84-1.74 (m, 1H), 0.77 (t, J=7.2 Hz, 3H); $^{13}$C NMR (100 MHz, CDCl$_3$) δ 166.84 (C=O), 148.82 (d, J=5.1 Hz, C), 133.51, 132.46, 132.36, 131.88, 131.85, 131.81, 131.72, 131.13, 129.74, 128.88, 128.52, 128.39, 128.31, 128.18, 126.51, 56.73 (CH), 52.01 (CH$_3$), 32.36 (d, J=3.6 Hz, CH$_2$), 10.41 (CH$_3$); IR (neat) 3172, 1720, 1280, 1186 cm$^{-1}$; HRMS (EI) Calculated for C$_{23}$H$_{24}$NO$_3$P: 393.1494. Found: 393.1500. The enantiomeric excess of 84% with R-isomer major was determined by HPLC (Chiralcel® AS-H column, Hexane/2-propanol=80:20; flow rate 1.0 mL/min; R-isomer, $t_R$ 18.40 min and S-isomer, $t_R$ 23.92 min).

TABLE 4

| Reaction example | Imine (10 mol %) | Reaction time (h) | Yield (%)$^a$ | e.e. (%)$^b$ | Byproduct Yield (%)$^c$ |
|---|---|---|---|---|---|
| 4-1 | 4a | 24 | (5a) 86 | 91 | (6a) 1 |
| 4-2$^d$ | 4a | 24 | (5a) 76 | 86 | (6a) 7 |
| 4-3$^e$ | 4a | 24 | (5a) 80 | 89 | — |
| 4-4 | 4b | 41 | (5b) 60 | 89 | (6b) 24 |
| 4-5 | 4c | 44 | (5c) 76 | 89 | (6c) 8 |
| 4-6 | 4d | 30 | (5d) 83 | 92 | (6d) 4 |
| 4-7 | 4e | 44 | (5e) 71 | 87 | (6e) 28 |
| 4-8$^f$ | 4e | 24 | (5e) 52 | 79 | (6e) 47 |
| 4-9 | 4f | 30 | (5f) 87 | 88 | (6f) 6 |
| 4-10 | 4g | 30 | (5g) 86 | 91 | — |
| 4-11 | 4h | 41 | (5h) 68 | 84 | (6h) 24 |
| 4-12 | 4i | 43 | (5i) 84 | 85 | (6i) 6 |
| 4-13 | 4j | 30 | (5j) 86 | 89 | (6j) 3 |
| 4-14 | 4k | 40 | (5k) 92 | 84 | — |

$^a$Based on imine.
$^b$Determined by HPLC, using Chiralcel ® OD-H, AD-H, or AS-H column.
$^c$Yield determined by $^1$H-NMR or HPLC.
$^d$Reaction using (+)-MINBOL.
$^e$Reaction using (+)-MINBOL (5 mol %) and β-amino alcohol compound 3a (5 mol).
$^f$Reaction without methanol (1.8 equivent).

REACTION EXAMPLE 5-1~5-4

The reaction scheme of enantioselective addition of organozinc to imines 4a, 4d, 4g, and 4j using the β-amino alcohol compounds 3a of the following reaction examples 5-1~5-17 are as follows:

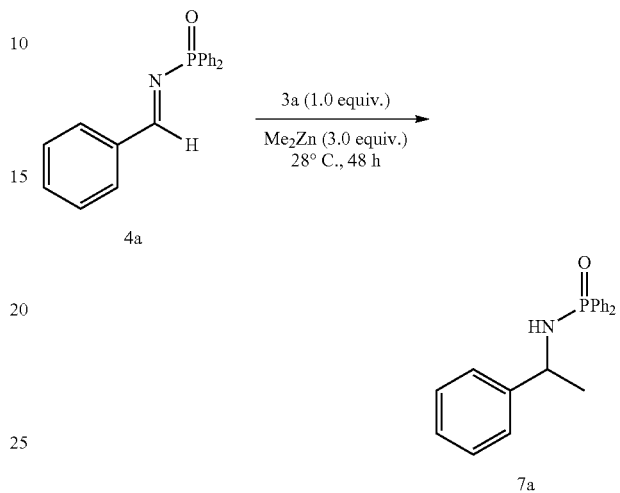

4a, 7a: Ar=phenyl
4d, 7d: Ar=4-toluene
4g, 7g: Ar=4-methoxyl-phenyl
4j, 7j: Ar=4-chlorophenyl

REACTION EXAMPLE 5-1

The imine 4a (0.34 mmol) and 3a (83.4 g, 0.34 mmol) were stirred for 5 min at 0° C. Me$_2$Zn in toluene (1.2 M, 0.85 mL, 1.02 mmol) was added dropwise to the mixture under ice-bath condition. The temperature was raised to room temperature (25-28° C.) and stirred for 48 h and the reaction was quenched with aqueous ammonium chloride (4.0 mL), and added hydrochloric acid (1.0 N) to acidify the solution (pH=2). The aqueous layer was extracted with CH$_2$Cl$_2$ (10 mL×3) and the organic layers were dried over anhydrous Na$_2$SO$_4$. Concentration and purification by column chromatography (EA/Hex=1:5-1:0) gave the corresponding addition product 7a (N-[1-(Phenyl)ethyl]-P,P-diphenylphosphinoylamide, white solid) with 96% yield and 96% enantiomeric excess (e.e.). $^1$H NMR (400 MHz, CDCl$_3$) δ 7.90-7.85 (m, 2H), 7.82-7.76 (m, 2H), 7.47-7.37 (m, 4H), 7.35-7.30 (m, 2H), 7.29-7.18 (m, 5H), 4.41-4.31 (m, 1H), 3.25-3.24 (m, 1H), 1.54 (d, J=6.8 Hz, 3H); $^{13}$C NMR (100 MHz, CDCl$_3$) δ 144.99 (d, J=6.6 Hz, C), 133.75, 132.40, 131.89, 131.79, 131.74, 131.68, 131.66, 131.41, 128.48, 128.46, 128.37, 128.34, 128.25, 127.02, 125.87, 50.96 (CH), 25.9 (d, J=2.9 Hz, CH$_3$); IR (neat) 3166, 1180 cm$^{-1}$; HRMS (FAB) Calculated for C$_{20}$H$_{21}$NOP ([M+H]$^+$): 322.1361. Found: 322.1367. The enantiomeric excess of 96% with R-isomer major was determined by HPLC (Chiralcel® OD-H column, Hexane/2-propanol=95:5; flow rate 1.0 mL/min; R-isomer, $t_R$ 11.66 min and S-isomer, $t_R$ 16.48 min).

REACTION EXAMPLE 5-2

The experimental procedure of this reaction example was the same as that illustrated in reaction example 5-1, except that the imime 4a was replaced by imine 4d. The reaction gave the corresponding addition product 7d (N-[1-(4-Methylphenyl)ethyl]-P,P-diphenylphosphinoylamide, white solid) with 88% yield and 96% enantiomeric excess (e.e.). $^1$H NMR (400 MHz, CDCl$_3$) δ 7.90-7.85 (m, 2H), 7.83-7.8 (m, 2H), 7.47-7.31 (m, 6H), 7.16-7.14 (m, 2H), 7.10-7.08 (m, 2H), 4.37-4.27 (m, 1H), 3.23-3.20 (m, 1H), 2.3 (s, 3H), 1.53 (d, J=6.4 Hz, 3H); $^{13}$C NMR (100 MHz, CDCl$_3$) δ 142.10 (d, J=6.6 Hz, C), 136.62, 133.80, 132.79, 132.41, 132.31, 131.89, 131.80, 131.73, 131.65, 131.49, 129.14, 128.45, 128.37, 128.32, 128.25, 125.78, 50.74 (CH), 25.87 (d, J=2.9 Hz, CH$_3$), 20.96 (CH$_3$); IR (neat) 3173, 1185 cm$^{-1}$; HRMS (EI) Calculated for C$_{20}$H$_{19}$NOP ([M-CH$_2$CH$_3$]$^+$): 320.1199. Found: 320.1203. The enantiomeric excess of 96% with R-isomer major was determined by HPLC (Chiralcel® OD-H column, Hexane/2-propanol=95:5; flow rate 0.8 mL/min; R-isomer, t$_R$ 12.60 min and S-isomer, t$_R$ 15.43 min).

REACTION EXAMPLE 5-3

The experimental procedure of this reaction example was the same as that illustrated in reaction example 5-1, except that the imime 4a was replaced by imine 4g. The reaction gave the corresponding addition product 7g (N-[1-(4-Methoxyphenyl)ethyl]-P,P-diphenylphosphinoylamide, white solid) with 78% yield and 97% enantiomeric excess (e.e.). $^1$H NMR (400 MHz, CDCl$_3$) δ 7.89-7.84 (m, 2H), 7.82-7.76 (m, 2H), 7.47-7.31 (m, 6H), 7.20-7.16 (m, 2H), 6.82-6.79 (m, 2H), 4.36-4.27 (m, 1H), 3.75 (s, 3H), 3.21-3.17 (m, 1H), 1.52 (d, J=6.4 Hz, 3H); $^{13}$C NMR (100 MHz, CDCl$_3$) δ 158.54, 137.25, 137.18, 132.54, 132.37, 131.89, 131.80, 131.72, 131.69, 131.64, 131.62, 131.58, 128.44, 128.36, 128.31, 128.23, 127.05, 113.80, 55.19 (CH$_3$), 50.39 (CH), 25.76 (CH$_3$); IR (neat) 3171, 1180 cm$^{-1}$; HRMS (EI) Calculated for C$_{20}$H$_{19}$NO$_2$P ([M-CH$_2$CH$_3$]$^+$): 366.1148. Found: 366.1151. The enantiomeric excess of 97% with R-isomer major was determined by HPLC (Chiralcel® AS-H column, Hexane/2-propanol=80:20; flow rate 1.0 mL/min; R-isomer, t$_R$ 17.63 min and S-isomer, t$_R$ 30.15 min).

REACTION EXAMPLE 5-4

The experimental procedure of this reaction example was the same as that illustrated in reaction example 5-1, except that the imime 4a was replaced by imine 4j. The reaction gave the corresponding addition product 7j (N-[1-(4-chlorophenyl)ethyl]-P,P-diphenylphosphinoylamide, white solid) with 93% yield and 96% enantiomeric excess (e.e.). The enantiomeric excess of 96% with R-isomer major was determined by HPLC (Chiralcel® OD-H column, Hexane/2-propanol=95:5; flow rate 1.0 mL/min; R-isomer, t$_R$ 14.49 min and S-isomer, t$_R$ 17.54 min).

The above examples are intended for illustrating the embodiments of the subject invention and the technical features thereof, but not for restricting the scope of protection of the subject invention. The scope of the subject invention is based on the claims as appended.

What is claimed is:

1. A method of enantioselective addition to imines, comprising: reacting R$_2$CH=NY with R$_3$ZnR$_4$ in the presence of a compound represented by the following formula (I),

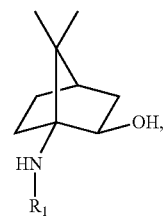

wherein
R$_1$ is alkyl or R$_6$;
each of R$_2$, R$_3$, and R$_4$ independently is alkyl, alkenyl, cycloalkyl, cycloalkenyl, heterocycloalkyl, heterocycloalkenyl, aryl, or heteroaryl;
Y is P(O)Ph$_2$; and
R$_6$ is selected from the group consisting of cycloalkyl, cycloalkenyl, heterocycloalkyl, heterocycloalkenyl, aryl, or heteroaryl.

2. The method as claimed in claim 1, wherein in formula (I),
R$_1$ is unsubstituted C$_{1-30}$ alkyl; C$_{1-30}$ alkyl substituted by one or more selected from the group consisting of halogen, cyano, C$_{1-30}$ alkoxy, C$_{1-30}$ haloalkyl, C$_{6-14}$ aryl, and 5-14 membered heteroaryl; —CH$_2$—R$_5$; or R$_6$;
wherein R$_5$ is selected from the group consisting of unsubstituted C$_{3-15}$ cycloalkyl; C$_{3-15}$ cycloalkyl substituted by one or more selected from the group consisting of halogen, cyano, C$_{1-30}$ alkoxy, C$_{1-30}$ haloalkyl, C$_{6-14}$ aryl, and 5-14 membered heteroaryl; unsubstituted C$_{3-15}$ cycloalkenyl; C$_{3-15}$ cycloalkenyl substituted by one or more selected from the group consisting of halogen, cyano, C$_{1-30}$ alkoxy, C$_{1-30}$ haloalkyl, C$_{6-14}$ aryl, and 5-14 membered heteroaryl; unsubstituted C$_{3-15}$ hetrocycloalkyl; C$_{3-15}$ hetrocycloalkyl substituted by one or more selected from the group consisting of halogen, cyano, C$_{1-30}$ alkoxy, C$_{1-30}$ haloalkyl, C$_{6-14}$ aryl, and 5-14 membered heteroaryl; unsubsttituted C$_{3-15}$ heterocycloalkenyl; and C$_{3-15}$ heterocycloalkenyl substituted by one or more selected from the group consisting of halogen, cyano, C$_{1-30}$ alkoxy, C$_{1-30}$ haloalkyl, C$_{6-14}$ aryl, and 5-14 membered heteroaryl;
R$_6$ is selected from the group consisting of unsubstituted C$_{3-15}$ cycloalkyl; C$_{3-15}$ cycloalkyl substituted by one or more selected from the group consisting of halogen, cyano, C$_{1-30}$ alkoxy, C$_{1-30}$ haloalkyl, C$_{6-14}$ aryl, and 5-14 membered heteroaryl; unsubstituted C$_{3-15}$ cycloalkenyl; C$_{3-15}$ cycloalkenyl substituted by one or more selected from the group consisting of halogen, cyano, C$_{1-30}$ alkoxy, C$_{1-30}$ haloalkyl, C$_{6-14}$ aryl, and 5-14 membered heteroaryl; unsubstituted C$_{3-15}$ hetrocycloalkyl; C$_{3-15}$ hetrocycloalkyl substituted by one or more selected from the group consisting of halogen, cyano, C$_{1-30}$ alkoxy, C$_{1-30}$ haloalkyl, C$_{6-14}$ aryl, and 5-14 membered heteroaryl; unsubsttituted C$_{3-15}$ heterocycloalkenyl; C$_{3-15}$ heterocycloalkenyl substituted by one or more selected from the group consisting of halogen, cyano, C$_{1-30}$ alkoxy, C$_{1-30}$ haloalkyl, C$_{6-14}$ aryl, and 5-14 membered heteroaryl; unsubstituted C$_{6-14}$ aryl; C$_{6-14}$ aryl substituted by one or more selected from the group consisting of halogen, cyano, C$_{1-30}$ alkoxy, C$_{1-30}$ haloalkyl, C$_{6-14}$ aryl, and 5-14 membered heteroaryl; unsubstituted 5-14 membered hetreoaryl; and 5-14 membered hetreoaryl substituted by one or more selected from the group consisting of halogen, cyano, $C_{1-30}$ alkoxy, $C_{1-30}$ haloalkyl, $C_{6-14}$ aryl, and 5-14 membered heteroaryl;

$R_2$ is unsubstituted or substituted $C_{1-30}$ alkyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl, and 5-14 membered heteroaryl; $(CH_2)_iR_a$; unsubstituted or substituted $C_{2-30}$ alkenyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl, and 5-14 membered heteroaryl; $(CH_2)_rCH=CH(CH_2)_kR_a$; unsubstituted or substituted $C_{5-14}$ cycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl; unsubstituted or substituted $C_{5-14}$ cycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl; unsubstituted or substituted 5-14 membered heterocycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl; unsubstituted or substituted 5-14 membered heterocycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl; unsubstituted or substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$alkyl, and $CO_2$—$C_{2-30}$ alkenyl; or unsubstituted or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl;

$R_3$ and $R_4$ independently is unsubstituted or substituted $C_{1-30}$ alkyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl, and 5-14 membered heteroaryl; unsubstituted or substituted $C_{2-30}$ alkenyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl, and $C_{5-14}$ heteroaryl; unsubstituted or substituted $C_{5-14}$ cycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl; unsubstituted or substituted $C_{5-14}$ cycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl; unsubstituted or substituted 5-14 membered heterocycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl; unsubstituted or substituted 5-14 membered heterocycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl; unsubstituted or substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl; or unsubstituted or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl;

$R_a$ is substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl; or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl; i is an integer of 1 to 30; and each of r and k independently is an integer of 0 to 30.

3. The method as claimed in claim 1, wherein in formula (I), $R_1$ is unsubstituted $C_{1-10}$ alkyl; $C_{1-10}$ alkyl substituted by one or more selected from the group consisting of halogen, cyano, $C_{1-10}$ alkoxy, $C_{1-10}$ haloalkyl; —$CH_2$—$R_5$; or $R_6$;

$R_5$ and $R_6$ are selected from the group consisting of unsubstituted $C_{3-15}$ cycloalkyl; $C_{3-15}$ cycloalkyl substituted by one or more selected from the group consisting of halogen, cyano, $C_{1-10}$ alkoxy, $C_{1-10}$ haloalkyl, $C_{6-14}$ aryl, and 5-14 membered heteroaryl; unsubstituted $C_{3-15}$ cycloalkenyl; $C_{3-15}$ cycloalkenyl substituted by one or more selected from the group consisting of halogen, cyano, $C_{1-10}$ alkoxy, $C_{1-10}$ haloalkyl, $C_{6-14}$ aryl, and 5-14 membered heteroaryl; unsubstituted $C_{3-15}$ hetrocycloalkyl; $C_{3-15}$ hetrocycloalkyl substituted by one or more selected from the group consisting of halogen, cyano, $C_{1-10}$ alkoxy, $C_{1-10}$ haloalkyl, $C_{6-14}$ aryl, and 5-14 membered heteroaryl; unsubsttituted $C_{3-15}$ heterocycloalkenyl; $C_{3-15}$ heterocycloalkenyl substituted by one or more selected from the group consisting of halogen, cyano, $C_{1-10}$ alkoxy, $C_{1-10}$ haloalkyl, $C_{6-14}$ aryl, and 5-14 membered heteroaryl; unsubstituted $C_{6-14}$ aryl; $C_{6-14}$ aryl substituted by one or more selected from the group consisting of halogen, cyano, $C_{1-10}$ alkoxy, $C_{1-10}$ haloalkyl, $C_{6-14}$ aryl, and 5-14 membered heteroaryl; unsubstituted 5-14 membered hetreoaryl; and 5-14 membered hetreoaryl substituted by one or more selected from the group consisting of halogen, cyano, $C_{1-10}$ alkoxy,$_{1-10}$ haloalkyl, $C_{6-14}$ aryl, and 5-14 membered heteroaryl;

$R_2$ is unsubstituted or substituted $C_{1-10}$ alkyl by one or more selected from the group consisting of $C_{6-14}$ aryl and 5-14 membered heteroaryl; $(CH_2)_iR_a$; unsubstituted or substituted $C_{2-10}$ alkenyl by one or more selected from the group consisting of $C_{6-14}$ aryl, and 5-14 membered heteroaryl; $(CH_2)_rCH=CH(CH_2)_kR_a$; unsubstituted $C_{5-14}$ cycloalkyl; unsubstituted $C_{5-14}$ cycloalkenyl; unsubstituted or substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl, and $CO_2$—$C_{2-10}$ alkenyl; or unsubstituted or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl, and $CO_2$—$C_{2-10}$ alkenyl;

R3 is unsubstituted $C_{1-10}$ alkyl;

R4 is unsubstituted or substituted $C_{1-10}$ alkyl by one or more selected from the group consisting of 5-14 membered heteroaryl, and $C_{6-14}$ aryl; unsubstituted or substituted $C_{2-10}$ alkenyl by one or more selected from the group consisting of $C_{6-14}$ aryl, and 5-14 membered heteroaryl; unsubstituted $C_{5-14}$ cycloalkyl; unsubstituted $C_{5-14}$ cycloalkenyl; unsubstituted or substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl, and $CO_2$—$C_{2-10}$ alkenyl; unsubstituted or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl, and $CO_2$—$C_{2-10}$ alkenyl;

$R_a$ is substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl, and $CO_2$—$C_{2-10}$ alkenyl; or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl, and $CO_2$—$C_{2-10}$ alkenyl;

i is an integer of 1 to 10; and each of r and k independently is an integer of 0 to 10.

4. The method as claimed in claim 1, wherein the compound represented by formula (I) is used in an amount of 0.05 to 1.5 equivents based on $R_2CH$=$NY$.

5. The method as claimed in claim 1, wherein $R_3ZnR_4$ is used in an amount of 1 to 10 equivents based on $R_2CH$=$NY$.

6. The method as claimed in claim 1, wherein $R_2CH$=$NY$ is reacted with $R_3ZnR_4$ in an aprotic solvent.

7. The method as claimed in claim 6, wherein the aprotic solvent is selected from the group consisting of n-hexane, toluene, dichloromethane, tetrahydrofuran, acetonitrile, a mixture of n-hexane and toluene, a mixture of n-hexane and dichloromethane, a mixture of n-hexane and tetrahydrofuran, and a mixture of n-hexane and acetonitrile.

8. The method as claimed in claim 6, wherein the aprotic solvent is selected from the group consisting of n-haxane, toluene, a mixture of n-hexane and toluene in a ratio of 1:1 to 1:5, a mixture of n-hexane and dichloromethane in a ratio of 1:1 to 1:3, a mixture of n-hexane and tetrahydrofuran in a ratio of 1:1 to 1:3, and a mixture of n-hexane and acetonitrile in a ratio of 1:1 to 1:3.

9. The method as claimed in claim 1, further comprising: adding an accelerator, wherein the accelerator is at least one selected from the group consisting of methanol, ethanol, isopropanol, triisopropylchlorosilane, trimethyl borate, triphenylphosphine oxide.

10. The method as claimed in claim 9, wherein the additive is used in an amount of 0.1 to 3 equivents based on $R_2CH$=$NY$.

* * * * *